(12) United States Patent
Kieval et al.

(10) Patent No.: US 8,620,422 B2
(45) Date of Patent: Dec. 31, 2013

(54) ELECTRODE ARRAY STRUCTURES AND METHODS OF USE FOR CARDIOVASCULAR REFLEX CONTROL

(75) Inventors: Robert S. Kieval, Medina, MN (US); Martin Rossing, Coon Rapids, MN (US); Adam Cates, Minneapolis, MN (US); Alejandro Covalin, Los Angeles, CA (US)

(73) Assignee: CVRx, Inc., Minneapolis, MN (US)

( * ) Notice: Subject to any disclaimer, the term of this patent is extended or adjusted under 35 U.S.C. 154(b) by 312 days.

(21) Appl. No.: 11/862,508

(22) Filed: Sep. 27, 2007

(65) Prior Publication Data

US 2008/0082137 A1    Apr. 3, 2008

Related U.S. Application Data

(60) Provisional application No. 60/827,242, filed on Sep. 28, 2006.

(51) Int. Cl.
*A61N 1/36* (2006.01)

(52) U.S. Cl.
USPC .......................................................... 607/2

(58) Field of Classification Search
USPC .......................................................... 607/2
See application file for complete search history.

(56) References Cited

U.S. PATENT DOCUMENTS

| | | |
|---|---|---|
| 5,341,807 A | 8/1994 | Nardella |
| 6,073,048 A | 6/2000 | Kieval et al. |
| 6,522,926 B1 | 2/2003 | Kieval et al. |
| 6,850,801 B2 | 2/2005 | Kieval et al. |
| 7,177,690 B2 | 2/2007 | Woods et al. |
| 7,206,640 B1 | 4/2007 | Overstreet |
| 7,221,981 B2 | 5/2007 | Gliner |
| 7,228,179 B2 | 6/2007 | Campen et al. |

(Continued)

FOREIGN PATENT DOCUMENTS

| | | |
|---|---|---|
| DE | 10 2004 012 564 A1 | 10/2005 |
| EP | 1 158 919 | 6/2005 |
| WO | WO 91/19531 | 12/1991 |
| WO | WO 03/076008 | 9/2003 |

OTHER PUBLICATIONS

International Search Report and Written Opinion of PCT Application No. PCT/US07/79881, dated Apr. 1, 2008, 10 pages total.
Supplementary European Search Report, dated Oct. 13, 2009.

(Continued)

*Primary Examiner* — Christopher D Koharski
*Assistant Examiner* — Jeremiah Kimball
(74) *Attorney, Agent, or Firm* — Patterson Thuente Pedersen, P.A.

(57) ABSTRACT

A tissue stimulation device includes an electrode array having at least four independently switchable electrodes. In one embodiment, the electrode array comprises a flexible base to which the electrodes are fixed that flexes to encompass at least a portion of an artery or other elongate biological structure. The electrodes are electrically coupled to and energized by a signal generator coupled to a control system. In one embodiment, the array of electrodes are configured such that a suitable signal pattern for stimulation pulses between or among a set of the switchable electrodes may be determined without having to reposition the electrode assembly by using a series of signal patterns activating different combinations of switchable electrodes in response to sub-stimulation test signals to determine a signal pattern that provides suitable patient response. In another embodiment, the array of electrodes includes an array of selectively activatable multi-polar electrodes.

10 Claims, 16 Drawing Sheets

(56) References Cited

U.S. PATENT DOCUMENTS

| | | | |
|---|---|---|---|
| 7,242,984 B2 | 7/2007 | DiLorenzo | |
| 7,245,970 B2* | 7/2007 | Zhu et al. | 607/28 |
| 7,254,445 B2 | 8/2007 | Law et al. | |
| 7,254,446 B1 | 8/2007 | Erickson et al. | |
| 7,263,402 B2 | 8/2007 | Thacker et al. | |
| 7,272,447 B2 | 9/2007 | Stett et al. | |
| 7,292,890 B2 | 11/2007 | Whitehurst et al. | |
| 7,295,876 B1 | 11/2007 | Erickson | |
| 7,315,763 B2 | 1/2008 | Kuzma et al. | |
| 7,317,944 B1 | 1/2008 | Overstreet | |
| 7,343,200 B2 | 3/2008 | Litvak et al. | |
| 2003/0060848 A1 | 3/2003 | Kieval et al. | |
| 2003/0060857 A1* | 3/2003 | Perrson et al. | 607/44 |
| 2004/0010303 A1 | 1/2004 | Bolea et al. | |
| 2004/0158298 A1 | 8/2004 | Gliner et al. | |
| 2005/0245970 A1 | 11/2005 | Erickson et al. | |
| 2005/0288729 A1 | 12/2005 | Libbus et al. | |
| 2006/0079945 A1 | 4/2006 | Libbus | |
| 2006/0173510 A1 | 8/2006 | Besio et al. | |
| 2006/0195145 A1 | 8/2006 | Lee et al. | |
| 2006/0195155 A1 | 8/2006 | Firlik et al. | |
| 2006/0259078 A1* | 11/2006 | Libbus | 607/2 |
| 2007/0043402 A1* | 2/2007 | Echauz et al. | 607/45 |
| 2007/0150007 A1 | 6/2007 | Anderson et al. | |
| 2007/0179565 A1 | 8/2007 | Overstreet et al. | |
| 2007/0179580 A1 | 8/2007 | Colborn | |
| 2007/0239228 A1 | 10/2007 | Bradley | |
| 2007/0239243 A1 | 10/2007 | Moffitt et al. | |
| 2007/0265679 A1 | 11/2007 | Bradley et al. | |
| 2008/0004673 A1 | 1/2008 | Rossing et al. | |
| 2008/0015669 A1 | 1/2008 | Jolly | |
| 2008/0021513 A1 | 1/2008 | Thacker et al. | |
| 2008/0046054 A1 | 2/2008 | Hjelle et al. | |
| 2008/0071325 A1 | 3/2008 | Bradley | |

OTHER PUBLICATIONS

Meyer, "Retina implant—a bioMEMs challenge," Sensors and Actuators, (2002), pp. 1-9, St. Ingbert, Germany.

European Search Report (EP10171133.1), dated Oct. 4, 2010.

\* cited by examiner

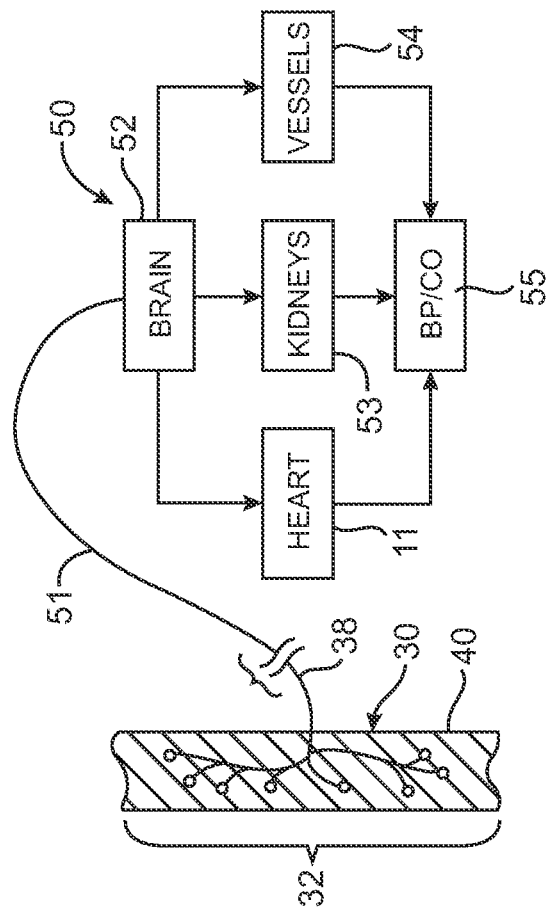
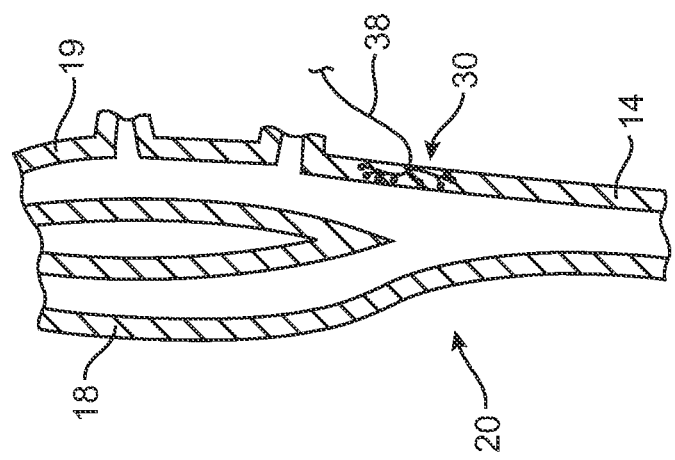
FIG. 2B
FIG. 2A

ELECTRODE ARRAY STRUCTURES AND METHODS OF USE FOR CARDIOVASCULAR REFLEX CONTROL

CROSS-REFERENCES TO RELATED APPLICATIONS

This application claims the benefit of Provisional Patent Application No. 60/827,242, filed Sep. 28, 2006, the disclosure of which is hereby incorporated by reference in its entirety.

BACKGROUND OF THE INVENTION

This invention relates generally to implantable medical devices. More particularly, the present invention relates to methods and apparatus for utilizing an electrode assembly having an array of electrodes as part of a baroreflex activation device.

Cardiovascular disease is a major contributor to patient illness and mortality. It also is a primary driver of health care expenditure, costing billions of dollars each year in the United States. Hypertension, or high blood pressure, is a major cardiovascular disorder that is estimated to affect 65 million people in the United Sates alone. Of those with hypertension, it is reported that fewer than 30% have their blood pressure under control. Hypertension is a leading cause of heart failure and stroke. It is the primary cause of death for tens of thousands of patients per year and is listed as a primary or contributing cause of death for hundreds of thousands of patients per year in the U.S. Accordingly, hypertension is a serious health problem demanding significant research and development for the treatment thereof.

Hypertension occurs when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Heart failure is the final common expression of a variety of cardiovascular disorders, including ischemic heart disease. It is characterized by an inability of the heart to pump enough blood to meet the body's needs and results in fatigue, reduced exercise capacity and poor survival. Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system activation in order to stop or at least minimize this vicious cycle and thereby treat or manage the heart failure.

A number of drug treatments have been proposed for the management of hypertension, heart failure and other cardiovascular disorders. These include vasodilators to reduce the blood pressure and ease the workload of the heart, diuretics to reduce fluid overload, inhibitors and blocking agents of the body's neurohormonal responses, and other medicaments.

Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month. Cardiac resynchronization therapy (CRT) may be used to improve the coordination of the heart's contractions. Other surgical procedures are available as well.

It is known that the wall of the carotid sinus, a structure at the bifurcation of the common carotid arteries, contains stretch receptors (baroreceptors) that are sensitive to the blood pressure. These receptors send signals via the carotid sinus nerve to the brain, which in turn regulates the cardiovascular system to maintain normal blood pressure (the baroreflex), in part through activation of the sympathetic nervous system. Electrical stimulation of the carotid sinus nerve (baropacing) has previously been proposed to reduce blood pressure and the workload of the heart in the treatment of high blood pressure and angina. For example, U.S. Pat. No. 6,073,048 to Kieval et al. discloses a baroreflex modulation system and method for stimulating the baroreflex are based on various cardiovascular and pulmonary parameters.

Another method of treating hypertension comprises electrical stimulation of the baroreceptors, a practice known as baroreflex activation therapy. U.S. Pat. No. 6,522,926 to Kieval, et al. discloses a baroreflex activation system and method for activating baroreceptors to regulate blood pressure. Implantable electrode assemblies for electrotherapy or electro-stimulation are well known in the art. For example, various configurations of implantable electrodes for an implantable baroreflex activation device are described in U.S. Published Application No. US 2004/0010303A1. One type of electrode assembly described therein is a surface-type stimulation electrode that includes a set of generally parallel elongate electrodes secured to, or formed on, a common substrate or base typically made of silicone or similar flexible, biocompatible material that is designed to be wrapped around and then typically sutured to the arterial wall. Prior to implantation in a patient, the electrodes are generally electrically isolated from one another. Once the electrode assembly is implanted, one or more of the electrodes are utilized as a cathode(s), while one or more of the remaining electrodes are utilized as an anode(s). The implanted cathode(s) and anode(s) are electrically coupled via the target region of tissue to be treated or stimulated.

The process of implanting the electrode assembly involves positioning the assembly such that the electrodes are properly situated against the arterial wall of the carotid sinus, and securing the electrode assembly to the artery so that the positioning is maintained. One example of mapping methods and techniques for implanting electrodes is disclosed in U.S. Pat. No. 6,850,801 to Kieval et al. The positioning is a critical step, as the electrodes must direct as much energy as possible toward the baroreceptors for maximum effectiveness and efficiency. The energy source for the implanted baroreflex stimulation device is typically an on-board battery with finite capacity, and it is desirable to provide a lower energy source to ensure patient safety. A high-efficiency implantation will provide a longer battery life and correspondingly longer effective service life between surgeries because less energy will be required to achieve the needed degree of therapy. As such, during implantation of the electrode assembly, the position of the assembly is typically adjusted several times during the implantation procedure in order to optimize the baroreflex response.

This process of adjusting and re-adjusting the position of the electrode assembly during implantation, known as mapping, adds to the overall procedure time. Present-day procedures involve positioning and holding the electrode assembly in place with forceps, hemostat or similar tool while applying the stimulus and observing the response in the patient. Movement by as little as 1 mm can make a medically relevant difference in the effectiveness of the baroreceptor activation.

Another challenge related to the positioning process is the task of keeping track of previous desirable positions. Because positioning the electrode assembly is an optimization procedure, surgeons will tend to search for better positions until they have exhausted all reasonable alternative positions. Returning the electrode assembly to a previously-observed optimal position can be quite difficult and frustrating, especially under surgical conditions.

After determining the optimal position, the surgeon must secure the electrode assembly in place. In an existing technique as described in U.S. Published Application No. US 2004/0010303A1, this is accomplished by wrapping finger-like elongated portions of the electrode assembly around the artery and suturing the assembly in place. The electrode assembly can be sutured to the arterial wall or to itself (after being wrapped around the artery). Loosening or removing the sutures, re-positioning the electrode assembly, and tightening or re-installing the sutures can increase the time and costs associated with the devices, and can also increase the risk of complications or surgeon errors related to protracted surgical procedures and fatigue.

In one embodiment disclosed in U.S. Published Application No. US 2004/0010303A1, an electrode array is described in which electrical paths through the tissue of the carotid sinus may be selectively defined by one or more pairs (bipolar) or groups (e.g., tripolar) of electrode pads in a multi-channel electrode array that is described in one embodiment as a four-by-four array of electrode pads. The electrode pads of the multi-channel electrode array are described as selectively activatable for purposes of mapping and targeting a specific area of the carotid sinus to determine the best combination of electrodes (e.g., individual pair, or group of pairs) to activate for maximum baroreflex responsiveness. The process for determining the best combination of electrodes as described involves conventional stimulation testing with the pairs or groups of pairs being stimulated with varying test patterns and the effectiveness of the baroreflex responsiveness being determined for each combination. While effective, this process can become lengthy and involved as the number of combinations of electrode pairs or groups of pairs being tested increases or if the electrode array is repositioned along the carotid sinus.

A further challenge facing current implantable baroreflex treatment devices is power usage. Often, baroreflex therapy is used in conjunction with drug therapy to treat hypertension, with the goal of reducing a patient's dependence on medication. When a patient first begins baroreflex therapy while still on medication, the amount of power required to induce a favorable baroreflex system response is relatively low. As the patient's reliance on medication becomes reduced, there can be a tendency to increase the baroreflex therapy by increasing the power of the stimulation. However, this negatively impacts battery life.

Accordingly, there exists a need for a baroreflex treatment that could deliver electrical stimulation and may be more easily implanted, adjusted or modified.

BRIEF SUMMARY OF THE INVENTION

A method and apparatus is disclosed for providing a baroreflex treatment that modulates the blood pressure of a patient by electrically stimulating a vessel wall, such as an artery or vein. A baroreflex activation device comprises an array of electrodes that are adapted to reduce the need to reposition the electrode array during surgery by allowing multiple selectively activatable electrode patterns. The baroreflex activation device is combined with a control system to automatically create a map of a patient's response to baroreflex stimulation and allow the device to be configured or reconfigured to optimize the patient's response. Further, the device allows the stimulation pattern to be adjusted or modified after implantation to account for any changes in the effectiveness of the treatment.

In one embodiment, the present invention provides a system and method for treating a patient by inducing a baroreflex signal to effect a change in the baroreflex system (e.g., altered autonomic nervous system activity, reduced heart rate, reduced blood pressure, etc.). The baroreflex signal is activated or otherwise modified by selectively activating baroreceptors in some embodiments, or afferent nerves emanating from baroreceptors in other embodiments. To accomplish this, the system and method of the present invention may utilize a baroreflex activation device positioned near a baroreceptor on the high-pressure side of the vasculature; such as in the carotid sinus, aortic arch, heart, common carotid arteries, subclavian arteries, brachiocephalic artery, pulmonary artery, great veins, peripheral veins or chamber(s) of the heart, or near the venous or low-pressure side of a patient's vasculature, such as the chambers in the heart, veins near the entrances to the atria, the pulmonary artery, the portal vein of the liver, the superior vena cava (SVC), the inferior vena cava (IVC), the jugular vein, the subclavian veins, the iliac veins, the femoral veins, and other peripheral areas of the vasculature where baroreceptor and baroreceptor-like receptors are found.

In one embodiment, the apparatus comprises a baroreflex activation device that includes an electrode array having at least four independently switchable electrodes. In one embodiment, the electrode array comprises a flexible base to which the electrodes are fixed that flexes to encompass at least a portion of an artery or other elongate biological structure. Once positioned about the structure, the electrodes of this embodiment are in intimate contact with the outer surface of the structure. At least one electrode serves as a cathode, and at least one electrode serves as an anode. The electrodes are electrically coupled to and energized by a signal generator coupled to a control system. The at least four independently switchable electrodes in the array of electrodes are configured such that a suitable signal pattern for stimulation pulses between or among a set of the switchable electrodes may be determined without having to reposition the electrode assembly; instead, a series of signal patterns activating different combinations of switchable electrodes to determine a signal pattern that provides suitable patient response.

In one embodiment, a surgeon wraps a baroreflex activation device having an array of electrodes that form an electrode assembly around a biological structure containing baroreceptors, such as an artery, with the electrodes in close proximity to the outer surface of the elongate biological structure. The device can determine an optimal electrode activation configuration or pattern without necessarily adjusting the physical position of the electrode assembly by, for example, providing a series of sub-stimulation test signals to differing electrode configurations or patterns on the electrode assembly, and observing the patient's response to the sub-stimulation test signals, wherein a sub-stimulation signal is one which does not create a medically meaningful baroreflex response in the patient to which the signal is applied. Once an optimal switching pattern of the array of electrodes of the baroreflex activation device is determined, the array can be initially set to use that pattern to provide therapy. Alternatively, the pattern may be recorded in the device to be repeated as appropriate for stimulation pulses to maintain the optimal therapeutic effect. After the device has been installed, if a physician subsequently wishes to modify the patient's response to stimulation pulses, the switching pattern of the electrode assembly can be changed as desired.

In one embodiment, the sub-stimulation test signals used to determine an optimum combination of electrodes in the electrode array include a high frequency signal that is delivered to a predetermined combination of electrode arrangements. The capacitance, inductance, resistance and/or reflectance of the high frequency signals are sampled for each test pattern combination to automatically create a sub-stimulation map of the anticipated responsiveness of each test pattern combination. Because the sub-stimulation map can be created without the required delay to determine the patient's physiological responsiveness to a given level of stimulation pulses for each given test pattern combination of electrodes, the present invention provides an improved approach for utilizing an electrode array as part of the electrode assembly of a baroreflex activation device.

In one embodiment, the results produced by the automatic testing of the sub-stimulation pulses are utilized to generate a single recommended combination of electrodes and polarities to be established as the pattern for stimulation pulses. In another embodiment, the results produced by the automatic testing generate a reduced set of combinations of electrodes and polarities, the effectiveness of which may then be confirmed by more conventional stimulation pulse testing and mapping. In another embodiment, the results produced by the automatic testing are stored within the device and the sub-stimulation test patterns may be repeated post implant by the physician or by the device itself to confirm/alter the recommended combination of electrodes and polarities.

In one embodiment, test pulses are provided and blood pressure or another physiologic parameter is monitored to identify an optimal response. An optimal response may comprise a response having the greatest absolute change in blood pressure, or a response having the most efficient change in blood pressure as determined by the amount of blood pressure change per unit of energy used, or a response having the most sustained effect on blood pressure, or a response having the fastest change in blood pressure.

In one embodiment, a variable electrode activation combination is utilized. The electrode activation combination may be continuously variable or periodically variable. In the case of a continuously variable electrode activation combination, a standard random number generator is coupled to a control system. The random number generator supplies random combinations of anode-cathode electrode pairs, thereby creating continuously variable electrode activation combinations. The electrode activation combination may also be periodically variable, wherein a period comprises a sequence of anode-cathode electrode activation combinations. The length of the period, and therefore the number of unique anode-cathode electrode activation combinations, may be adjusted as desired. In one embodiment, the periodically variable electrode activation combination comprises the favorable electrode activation combinations identified from the sub-stimulation signal testing previously discussed.

In another embodiment, the baroreflex activation device comprises a flexible base and an array of multi-pole electrodes that are independently activatable. Multi-pole electrodes comprise a center portion surrounded by two or more electrically conductive rings. Activation of a multi-pole electrode, such as between the center and an outer ring or between the inner ring and the outer ring, creates a spatially limited electric field. Such an activation can assist in controlling the depth of stimulation, so as to stimulate different tissues at different depths. Various parameters of such a multi-polar electrode embodiment may be modified or adjusted to affect the shape and penetrating depth of the stimulating electric field so as to provide the desired baroreflex therapy. In one aspect of this embodiment, the polarity is switchable between the various parts of the multi-polar electrode. For example, the center portion may comprise an anode, while the surrounding concentric rings comprise cathodes, or vice versa. The inner ring may comprise a cathode while the outer ring and central portion comprise anodes.

In another aspect of this embodiment, the multi-polar electrodes include a shielding portion or ground plane, to isolate the electrode from proximate electrodes. The shielding portion may comprise an outer-most ring surrounding an individual electrode, or the shielding portion may comprise a structure partly or substantially shielding multiple electrodes from one another.

In another embodiment of the present invention, the control signal generated by the control system comprises multiple successive pulses. In contrast to a control signal comprising a pulse waveform having a large amplitude, multiple pulses of smaller amplitude, called a pulse series, are fired in succession. Each pulse in the pulse series has a smaller amplitude, thereby yielding a similarly effective result to the large single pulse, however less power is required, thereby conserving battery usage. The pulse series may be fired between the same anode-cathode combination, or unique anode-cathode combinations may be used for each pulse in a pulse series. Similarly, successive pulse series may comprise identical or varied anode-cathode firing combinations. In an embodiment where each pulse in a pulse series fires between unique anode-cathode combinations, each successive pulse in the series may be staggered so as to overlap. Alternatively, each successive pulse in the series may be staggered such that there is no overlap between pulses.

To address hypertension and other conditions requiring blood pressure augmentation, the present invention provides electrode designs and methods configured to reduce the need to reposition an electrode activation device during surgery. By allowing multiple selectively activatable electrode patterns and combining the baroreflex activation device with a control system, the present invention can automatically create a map of a patient's response to baroreflex stimulation and allow the device to be configured or reconfigured to optimize the patient's response.

BRIEF DESCRIPTION OF THE DRAWINGS

The invention may be more completely understood in consideration of the following detailed description of various embodiments of the invention in connection with the accompanying drawings, in which:

FIG. 2A is a cross-sectional schematic illustration of the carotid sinus and baroreceptors within the vascular wall.

FIG. 2B is a schematic illustration of baroreceptors within the vascular wall and the baroreflex system.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
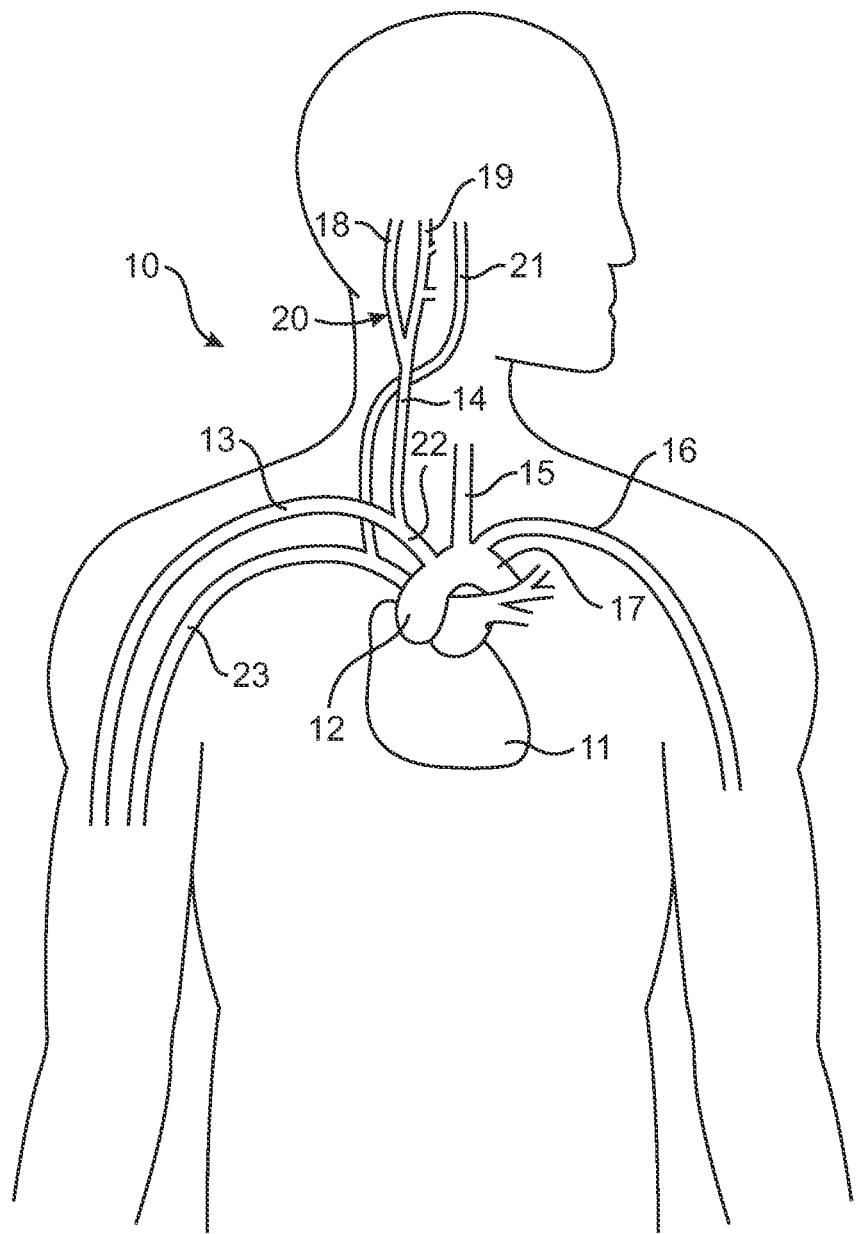
FIG. 1 is a schematic illustration of the upper torso of a human body showing the major arteries and veins and associated anatomy.

To better understand the present invention, it may be useful to explain some of the basic vascular anatomy associated with the cardiovascular system. Refer to FIG. 1 which is a schematic illustration of the upper torso of a human body 10 showing some of the major arteries and veins of the cardiovascular system. The left ventricle of the heart 11 pumps oxygenated blood up into the aortic arch 12. The right subclavian artery 13, the right common carotid artery 14, the left common carotid artery 15 and the left subclavian artery 16 branch off the aortic arch 12 proximal of the descending thoracic aorta 17. Although relatively short, a distinct vascular segment referred to as the brachiocephalic artery 22 connects the right subclavian artery 13 and the right common carotid artery 14 to the aortic arch 12. The right carotid artery 14 bifurcates into the right external carotid artery 18 and the right internal carotid artery 19 at the right carotid sinus 20. Although not shown for purposes of clarity only, the left carotid artery 15 similarly bifurcates into the left external carotid artery and the left internal carotid artery at the left carotid sinus.

From the aortic arch 12, oxygenated blood flows into the carotid arteries 15, 18/19 and the subclavian arteries 13/16. From the carotid arteries 18/19, oxygenated blood circulates through the head and cerebral vasculature and oxygen depleted blood returns to the heart 11 by way of the jugular veins, of which only the right internal jugular vein 21 is shown for sake of clarity. From the subclavian arteries 13/16, oxygenated blood circulates through the upper peripheral vasculature and oxygen depleted blood returns to the heart by way of the subclavian veins, of which only the right subclavian vein 23 is shown, also for sake of clarity. The heart 11 pumps the oxygen depleted blood through the pulmonary system where it is re-oxygenated. The re-oxygenated blood returns to the heart 11 which pumps the re-oxygenated blood into the aortic arch as described above, and the cycle repeats.

Within the arterial walls of the aortic arch 12, common carotid arteries 14/15 (near the right carotid sinus 20 and left carotid sinus), subclavian arteries 13/16, brachiocephalic artery 22, and other arteries, veins and cardiac structures, there are baroreceptors 30. For example, as best seen in FIG. 2A, within the walls of many veins, the pulmonary vasculature and the chambers of the heart, as in the walls of the carotid sinus, aorta and other arterial structures, there are baroreceptors 30. Baroreceptors 30 are a type of stretch receptor used by the body to sense blood pressure and blood volume. An increase in blood pressure or volume causes the vascular wall to stretch, and a decrease in blood pressure or volume causes the vascular wall to return to its original size. In many vessels, such a cycle is repeated with each beat of the heart. In others, in particular some of the body's veins, the pressure and volume change more slowly. Because baroreceptors 30 are located within the vascular wall, they are able to sense deformation of the adjacent tissue, which is indicative of a change in blood pressure or volume. The baroreceptors 30 located in the right carotid sinus 20, the left carotid sinus and the aortic arch 12 play the most significant role in sensing blood pressure that affects the baroreflex system 50, which is described in more detail with reference to FIG. 2B.

Refer now to FIG. 2B, which shows a schematic illustration of baroreceptors 30 disposed in a generic vascular wall 40 and a schematic flow chart of the baroreflex system 50. Baroreceptors 30 are profusely distributed within the vascular walls discussed previously, and generally form an arbor 32. The baroreceptor arbor 32 comprises a plurality of baroreceptors 30, each of which transmits baroreceptor signals to the brain 52 via nerve 38. The baroreceptors 30 are so profusely distributed and arborized within the vascular wall 40 that discrete baroreceptor arbors 32 are not readily discernable. To this end, those skilled in the art will appreciate that the baroreceptors 30 shown in FIG. 2B are primarily schematic for purposes of illustration and discussion.

The present invention is suitable for use with various medical devices such as tissue stimulation devices, systems, and methods, as well as monitoring devices. Tissue stimulation therapies can be used to stimulate nerves, including nerve endings and other neural structures, or receptors, such as baroreceptors, pressoreceptors, mechanoreceptors, stretch receptors and chemoreceptors, or other excitable tissues, or any other tissue of a patient. Although many of the embodiments described herein refer to stimulating tissues such as baroreceptors associated with the cardiovascular system, the present invention is also suitable for use with embodiments wherein cranial tissues, deep brain tissues, or spinal tissues are stimulated or other tissues. Tissue stimulation can be useful for treating various maladies and conditions, including but not limited to pain, sleep disorders, hypertension, hypotension, and other conditions.

In general, cardiovascular receptors may be sensitive to pressure and/or mechanical deformation and are referred to as baroreceptors, mechanoreceptors, pressoreceptors, stretch receptors, and the like. For cardiovascular and renal therapies, the present invention is intended to activate or otherwise interact with any or all of these types of receptors and/or nerve fibers from the receptors so long as such activation or interaction results in modulation of the reflex control of the patient's circulation. While there may be small structural or anatomical differences among various receptors in the vasculature, for the purposes of the present invention, activation may be directed at any of these receptors and/or nerves and/or nerve endings from these receptors so long as they provide the desired effects. In particular, such receptors will provide afferent signals, i.e., signals to the brain, which provide the blood pressure and/or volume information to the brain. This allows the brain to cause "reflex" changes in the autonomic nervous system, which in turn modulate organ activity to maintain desired hemodynamics and organ perfusion. For convenience, the term "baroreceptor" will be used to refer to any or all of such receptors, in the arterial or venous systems, unless otherwise expressly noted. Stimulation of the baroreflex system may be accomplished by stimulating such receptors, nerves, nerve fibers, or nerve endings, or any combination thereof.

For discussion purposes, it will be assumed that baroreceptors 30 are connected to the brain 52 via the nervous system 51. Thus, the brain 52 is able to detect changes in blood pressure which are indicative of cardiac output and/or blood volume. If cardiac output and/or blood volume are insufficient to meet demand (i.e., the heart 11 is unable to pump sufficient blood), the baroreflex system 50 activates a number of body systems, including the heart 11, kidneys 53, vessels 54, and other organs/tissues. Such activation of the baroreflex system 50 generally corresponds to an increase in neurohormonal activity. Specifically, the baroreflex system 50 initiates a neurohormonal sequence that signals the heart 11 to increase heart rate and increase contraction force in order to increase cardiac output, signals the kidneys 53 to increase blood volume by retaining sodium and water, and signals the vessels 54 to constrict to elevate blood pressure. The cardiac, renal and vascular responses increase blood pressure and cardiac output 55, and thus increase the workload of the heart 11. In a patient with heart failure, this further accelerates myocardial damage and exacerbates the heart failure state.

The ability to control the baroreflex response and cardiovascular, renal, and neurological function, by intervention on the low-pressure side of the vasculature is advantageous in several respects. Intervention on the venous and cardiopulmonary side of the vasculature reduces the risk of organ damage, including stroke, from systemic arterial thromboembolism. Moreover, the devices and structures used for intervening on the venous and cardiopulmonary side of the vasculature may be less complicated since the risk they pose to venous circulation is much less than to arterial circulation. Additionally, the availability of venous and cardiopulmonary baroreceptors allows placement of electrodes and other devices which reduce the risk of unwanted tissue stimulation resulting from current leakage to closely adjacent nerves, muscles, and other tissues.

To address the problems of hypertension, heart failure, other cardiovascular disorders and renal disorders, the present invention provides a number of devices, systems and methods by which the baroreflex system 50 is activated to reduce excessive blood pressure, autonomic nervous system activity and neurohormonal activation. In particular, the present invention provides a number of devices, systems and methods by which baroreceptors 30 may be activated in some embodiments or afferent nerves emanating from baroreceptors 30 may be activated in other embodiments, thereby mimicking an increase in blood pressure and signaling the brain 52 to reduce the body's blood pressure and level of sympathetic nervous system and neurohormonal activation, and increase parasympathetic nervous system activation, thus having a beneficial effect on the cardiovascular system and other body systems.

Figure 3:
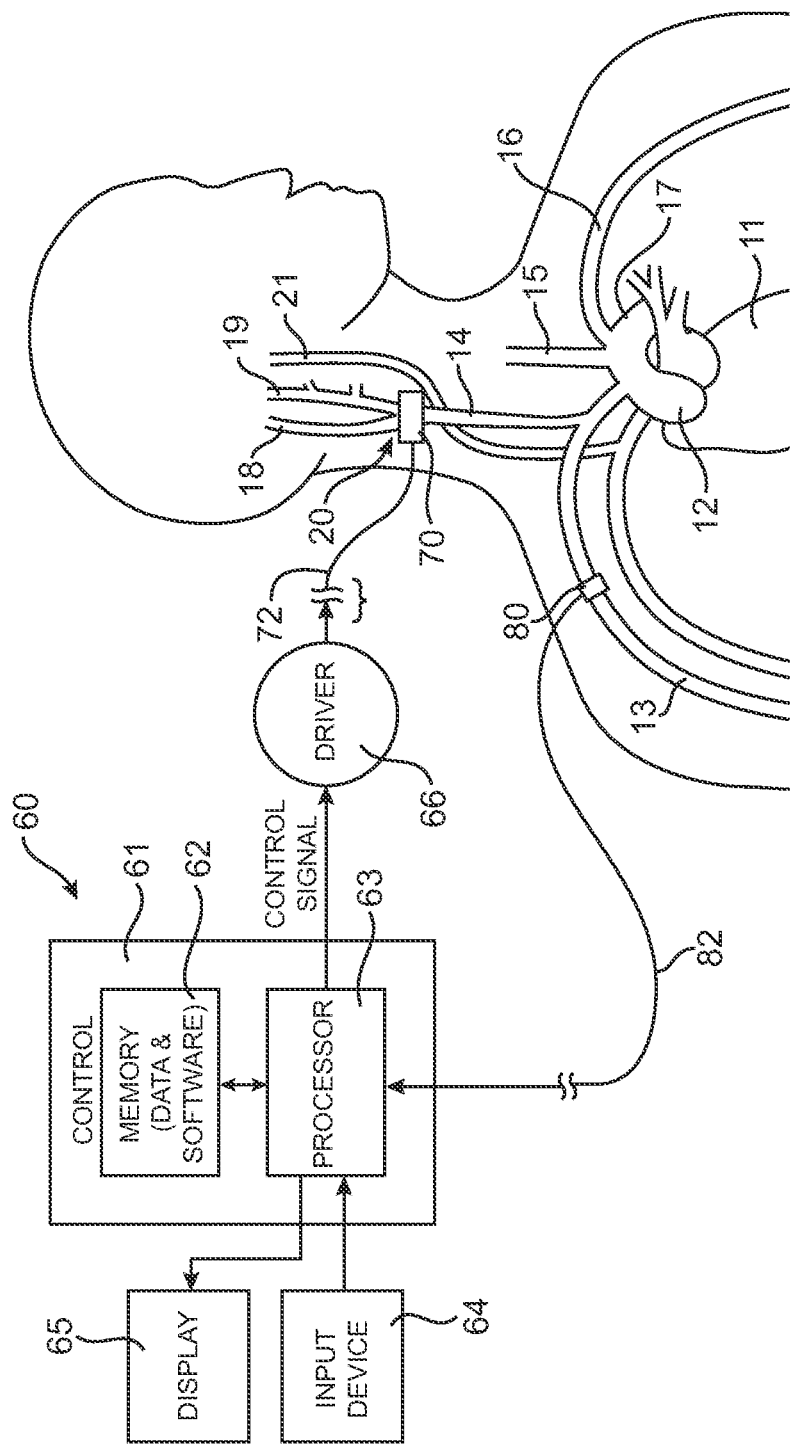
FIG. 3 is a schematic illustration of a tissue stimulation system according to an embodiment of the present invention.

With reference to FIG. 3, the present invention generally provides a system including a control system 60, a tissue stimulation (or baroreflex activation) device 70, and one or more sensor(s) 80 (optional), which generally operate in the following manner. The sensor(s) 80 optionally senses and/or monitors a parameter (e.g., cardiovascular function) indicative of the need to modify the baroreflex system and generates a signal indicative of the parameter. The control system 60 generates a control signal as a function of the received sensor signal. The control signal activates, deactivates or otherwise modulates the baroreflex activation device 70. Typically, activation of the device 70 results in activation of the baroreceptors 30. Alternatively, deactivation or modulation of the baroreflex activation device 70 may cause or modify activation of the baroreceptors 30 or the afferent nerves emanating from baroreceptors 30. The baroreflex activation device 70 may comprise a wide variety of devices which utilize electrical or non-electrical means to activate baroreceptors 30. Thus, when the sensor 80 detects a parameter indicative of the need to modify the baroreflex system activity (e.g., excessive blood pressure), the control system 60 generates a control signal to modulate (e.g., activate) the baroreflex activation device 70 thereby inducing a baroreceptor 30 signal that is perceived by the brain 52 to be apparent excessive blood pressure. When the sensor 80 detects a parameter indicative of normal body function (e.g., normal blood pressure), the control system 60 generates a control signal to modulate (e.g., deactivate) the baroreflex activation device 70.

Embodiments of the baroreflex activation device 70 are suitable for implantation, and are preferably implanted using a minimally invasive percutaneous translumenal approach and/or a minimally invasive surgical approach, depending on whether the device 70 is disposed intravascularly, extravascularly, transvascularly, or within the vascular wall 40. The baroreflex activation device 70 may be positioned anywhere baroreceptors 30 affecting the baroreflex system 50 are numerous, such as in the heart 11, in the aortic arch 12, in the common carotid arteries 18/19 near the carotid sinus 20, in the subclavian arteries 13/16, brachiocephalic artery 22, or in the pulmonary artery, veins, or heart. The baroreflex activation device 70 may be implanted such that the device 70 is positioned immediately adjacent the baroreceptors 30. Alternatively, the baroreflex activation device 70 may be outside the body such that the device 70 is positioned a short distance from but proximate to the baroreceptors 30. Preferably, the baroreflex activation device 70 is implanted near the right carotid sinus 20 and/or the left carotid sinus (near the bifurcation of the common carotid artery) and/or the aortic arch 12, where baroreceptors 30 have a significant impact on the baroreflex system 50. For purposes of illustration only, the present invention is described with reference to baroreflex activation device 70 positioned near the carotid sinus 20.

The optional sensor 80 is operably coupled to the control system 60 by electric sensor cable or lead 82. The sensor 80 may comprise any suitable device that measures or monitors a parameter (physiologic or otherwise) indicative of the need to modify the activity of the baroreflex system. For example, the sensor 80 may comprise a physiologic transducer or gauge that measures ECG, blood pressure (systolic, diastolic, average or pulse pressure), blood volumetric flow rate, blood flow velocity, blood pH, O2 or CO2 content, pulse rate, mixed venous oxygen saturation (SVO2), vasoactivity, nerve activity, tissue activity, body movement, body temperature, activity levels, respiration, or composition. Examples of suitable transducers or gauges for the sensor 80 include ECG electrodes, a piezoelectric pressure transducer, an ultrasonic flow velocity transducer, an ultrasonic volumetric flow rate transducer, a thermodilution flow velocity transducer, a capacitive pressure transducer, a membrane pH electrode, an optical detector (SVO2), tissue impedance (electrical), a pulse oximetry sensor, or a strain gauge. Although only one sensor 80 is shown, multiple sensors 80 of the same or different type at the same or different locations may be utilized.

In some embodiments, sensor 80 may be positioned in a chamber of the heart 11, or in/on a major artery such as the aortic arch 12, a common carotid artery 14/15, a subclavian artery 13/16 or the brachiocephalic artery 22, such that the parameter of interest may be readily ascertained. The sensor 80 may be disposed inside the body such as in or on an artery, a vein or a nerve (e.g. vagus nerve), or disposed outside the body, depending on the type of transducer or gauge utilized. The sensor 80 may be separate from the baroreflex activation device 70 or combined therewith. For purposes of illustration only, the sensor 80 is shown positioned on the right subclavian artery 13 in FIG. 3, and on the patient's head in FIG. 5.

By way of example, the control system 60 includes a control block 61 comprising a processor 63 and a memory 62. Control system 60 is connected to the sensor 80 by way of sensor cable 82. Control system 60 is also connected to the baroreflex activation device 70 by way of electric control cable 72. Thus, the control system 60 receives a sensor signal from the sensor 80 by way of sensor cable 82, and transmits a control signal to the baroreflex activation device 70 by way of control cable 72.

The memory 62 may contain data related to the sensor signal, the control signal, and/or values and commands provided by the input device 64. The memory 62 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold or stimulation value, rises above an upper predetermined threshold or stimulation value or when the sensor signal indicates a specific physiologic event.

The control system 60 may operate as a closed loop utilizing feedback from the sensor 80, or other sensors, such as heart rate sensors which may be incorporated or the electrode assembly, or as an open loop utilizing reprogramming commands received by input device 64. The closed loop operation of the control system 60 preferably utilizes some feedback from the transducer 80, but may also operate in an open loop mode without feedback. Programming commands received by the input device 64 may directly influence the control signal, the output activation parameters, or may alter the software and related algorithms contained in memory 62. The treating physician and/or patient may provide commands to input device 64. In one embodiment, a display 65 may be used to view the sensor signal, control signal and/or the software/data contained in memory 62.

The control signal generated by the control system 60 may be continuous, periodic, alternating, episodic or a combination thereof, as dictated by an algorithm contained in memory 62. Continuous control signals include a constant pulse, a constant train of pulses, a triggered pulse and a triggered train of pulses. Examples of periodic control signals include each of the continuous control signals described above which have a designated start time (e.g., beginning of each period as designated by minutes, hours, or days in combinations of) and a designated duration (e.g., seconds, minutes, hours, or days in combinations of). Examples of alternating control signals include each of the continuous control signals as described above which alternate between the right and left output channels or which vary in some other aspect of the control parameter such as frequency, amplitude, pattern or waveform. Examples of episodic control signals include each of the continuous control signals described above which are triggered by an episode (e.g., activation by the physician/patient, an increase/decrease in blood pressure above a certain threshold, heart rate above/below certain levels, changes in patient posture, activity level, etc.).

Figure 4:
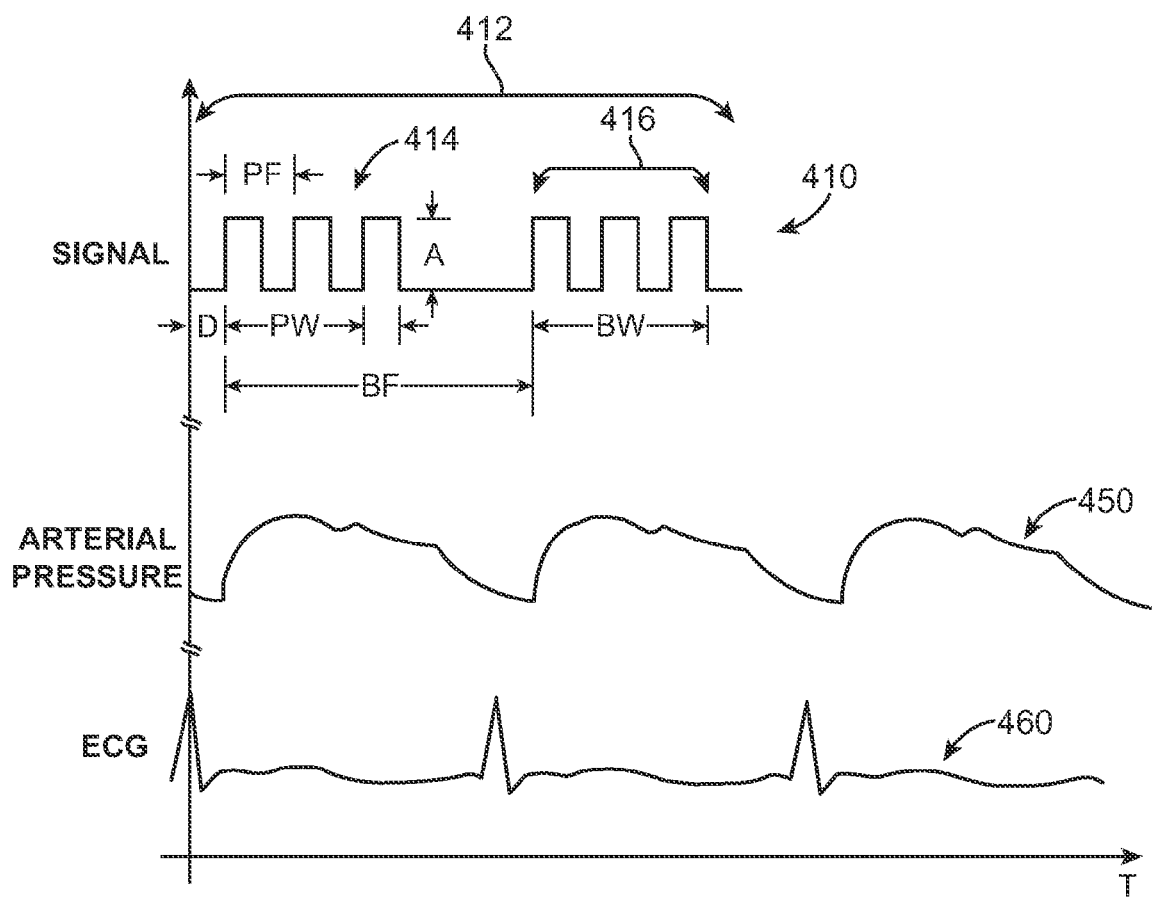
FIG. 4 is an illustration of an arterial pressure signal, an electrocardiogram signal, and a control/output signal as a function of time.

In electrical activation embodiments wherein the output signal comprises a pulse train, several other signal characteristics may be changed in addition to the pulse characteristics described above. As illustrated in FIG. 4, the control or output signal 410 may comprise a pulse train 412 which generally includes a series of pulses 414 occurring in bursts 416. Pulse train 412 characteristics which may be changed include, but are not limited to: burst amplitude (equal to pulse amplitude if constant within burst packet 416), burst waveform (i.e., pulse amplitude variation within burst packet 416), burst frequency (BF), and burst width or duration (BW). The signal 410 or a portion thereof (e.g., burst 416 within the pulse train 412) may be triggered by any of the events discussed previously, or by a particular portion of the arterial pressure signal 450 or the ECG signal 460 (e.g., R wave as shown in FIG. 4, or phase of respiration, etc), or another physiologic timing indicator. If the signal 410 or a portion thereof is triggered, the triggering event may be changed and/or the delay from the triggering event may be changed.

The control system 60 may be implanted in whole or in part. For example, the entire control system 60 may be carried externally by the patient utilizing transdermal connections to the sensor lead 82 and the control lead 72. Alternatively, the control block 61 and driver 66 may be implanted with the input device 64 and display 65 carried externally by the patient utilizing transdermal connections therebetween. As a further alternative, the transdermal connections may be replaced by cooperating transmitters/receivers to remotely communicate between components of the control system 60 and/or the sensor 80 and baroreflex activation device 70.

Figure 5:
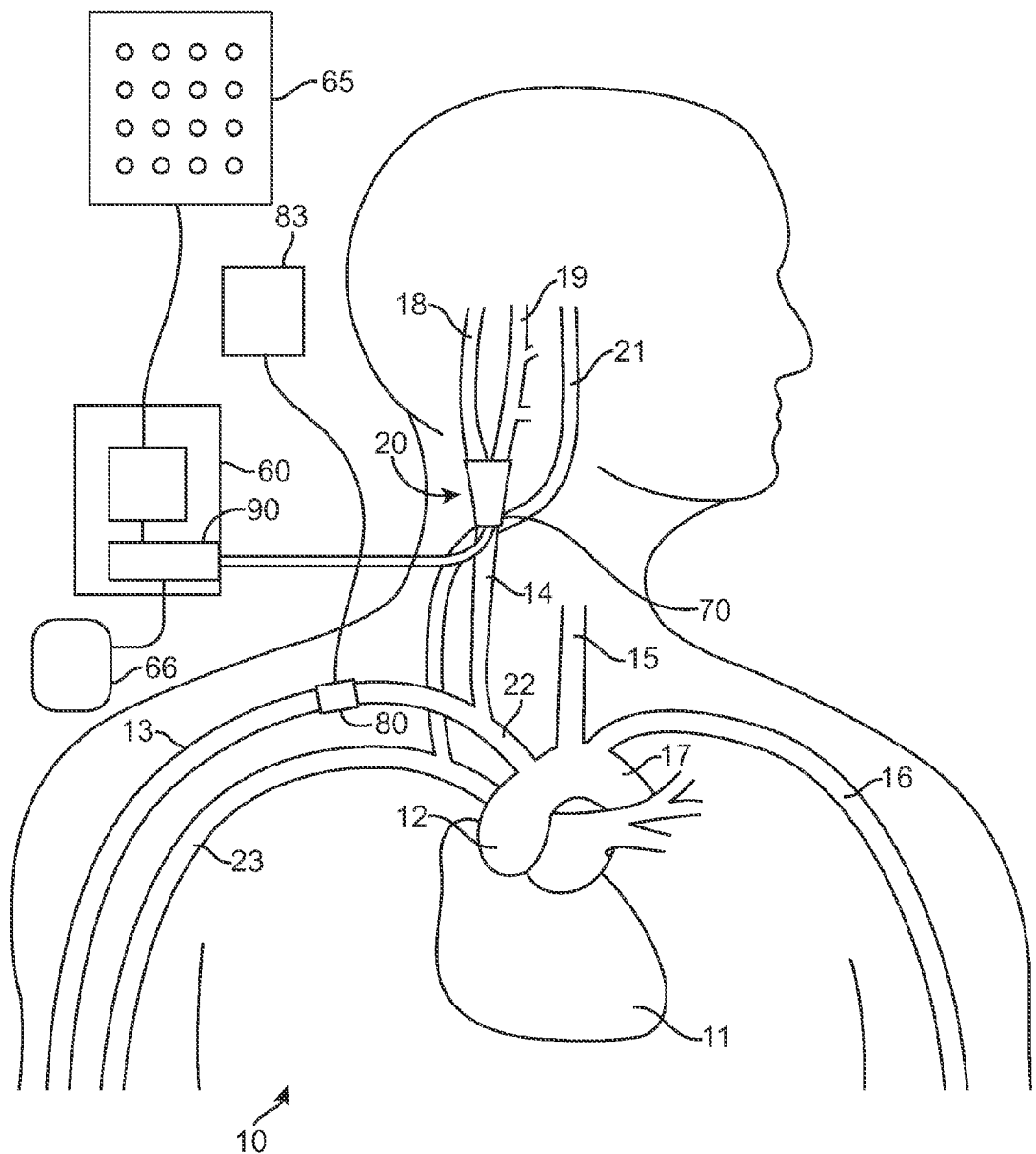
FIG. 5 is a schematic illustration of a tissue stimulation system according to an embodiment of the present invention.
Figure 6:
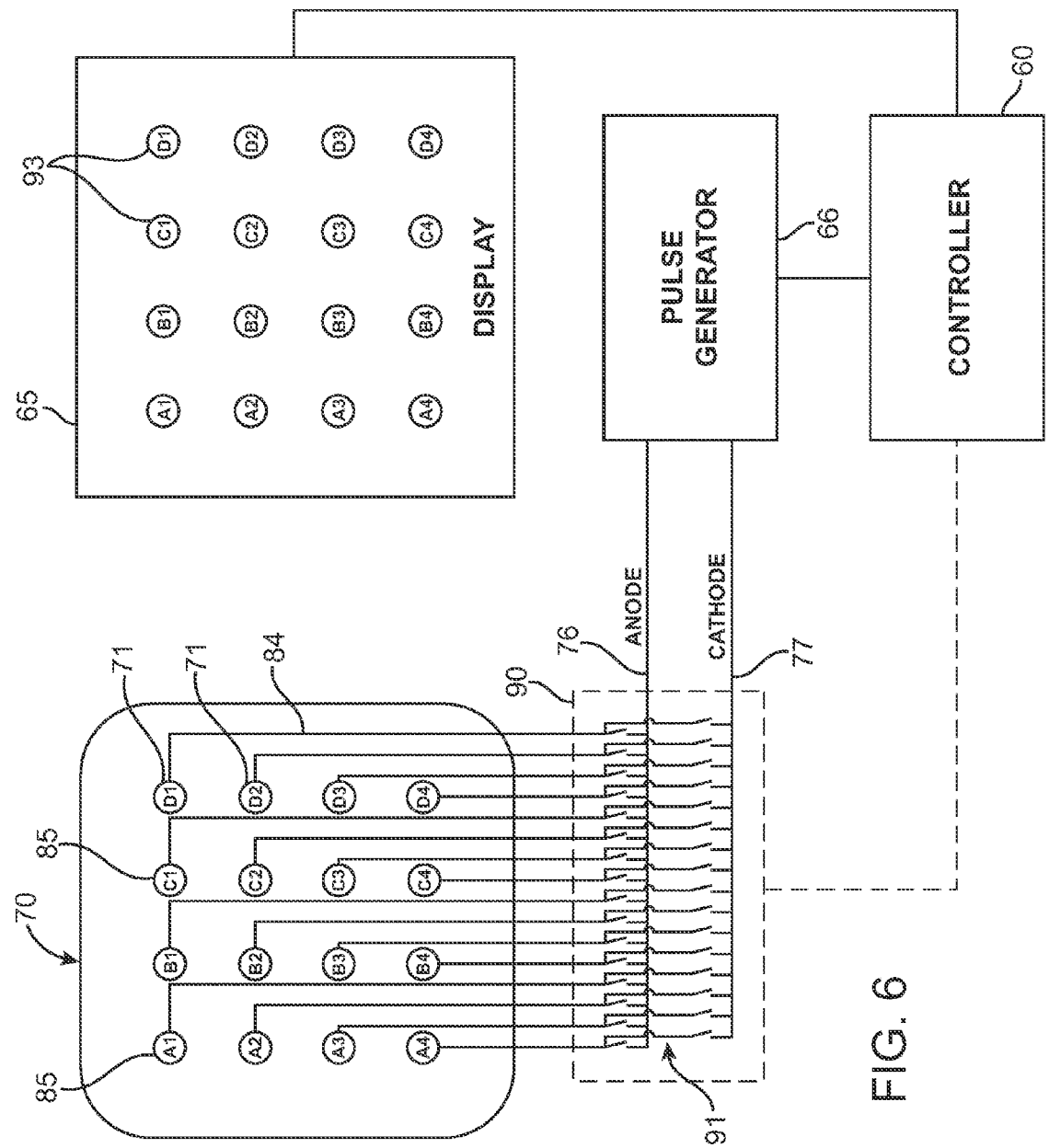
FIG. 6 is a schematic illustration of a tissue stimulation system according to an embodiment of the present invention.
Figure 7:
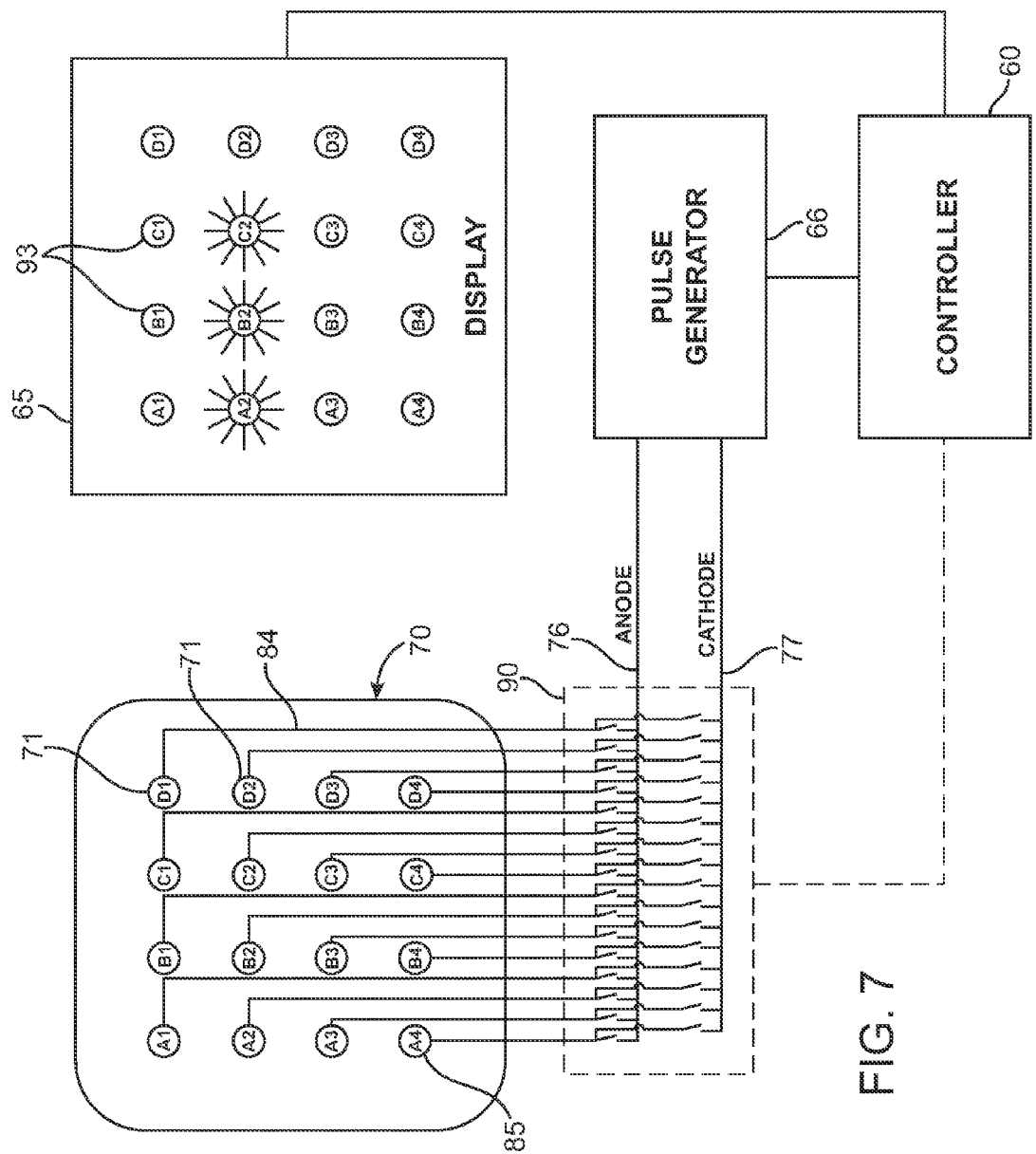
FIG. 7 is a schematic illustration of a tissue stimulation system according to an embodiment of the present invention.
Figure 8:
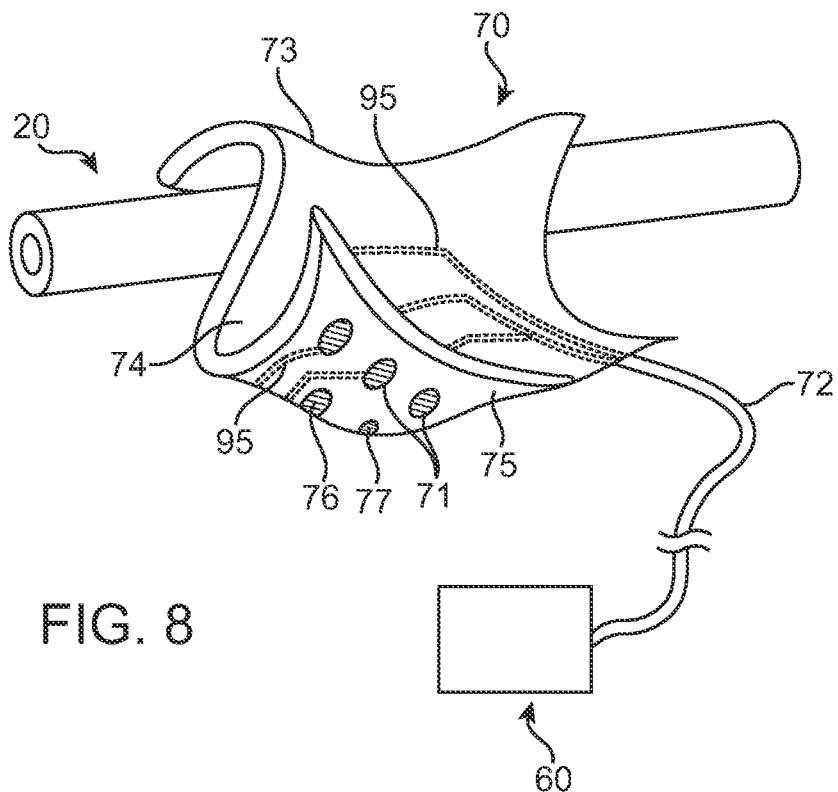
FIG. 8 is a perspective view of a tissue stimulation device according to an embodiment of the present invention, partially installed on an artery.

Referring now to FIGS. 5-8, one embodiment of the present invention is depicted. A baroreflex activation device 70 comprises an electrode array having a generally flexible elastomeric base 73 and a plurality of electrodes 71. Baroreflex activation device 70 is wrapped around a patient's artery or similar structure, such as carotid sinus 20, such that the electrodes 71 are in contact with carotid sinus 20. Baroreflex activation device 70 is generally operably coupled to control system 60. In the present embodiment, baroreflex activation device 70 is operably coupled to a switching mechanism 90, which may or may not be physically located within control system 60. A driver 66 is included, which may or may not be physically located within control system 60. A display 65 may communicate which electrodes 71 are being activated. A sensor 80 is provided, which may be coupled to a monitor 83 as depicted in FIG. 5, or may be coupled to control system 60 as depicted in FIG. 3.

Driver 66 is operably coupled to electrodes 71, and produces an electrical control signal by creating an electric potential difference between two or more electrodes. Driver 66 may comprise a power amplifier, pulse generator, or the like to selectively deliver electrical control signals to electrodes 71. In a preferred embodiment, driver 66 comprises a pulse generator. The electrical control signal generated by pulse generator 66 may be continuous, periodic, episodic, or a combination thereof, as dictated by an algorithm contained in memory 62 of control system 60. Continuous control signals include a constant pulse, a constant train of pulses, a triggered pulse and a triggered train of pulses. Periodic control signals include each of the continuous control signals described above which have a designated start time and a designated duration. Episodic control signals include each of the continuous control signals described above which are triggered by an episode.

Electrode array 70 includes a generally flexible elastomeric base 73 having a pair of opposing major surfaces 74 and 75. The base 73 is designed to conform at least partially around an outer surface of an artery or similar structure when baroreflex activation device 70 is installed thereupon. A plurality of electrodes 71 are provided on or near at least one of surfaces 74 and 75. Baroreflex activation device 70 is operably coupled generally to control system 60 with connecting lead 72. Individual electrodes 71 may be coupled to lead 72 with individual conductors 95 embedded within flexible base 73, or with conductive traces similar to a printed circuit board, or with conductive materials, or other similar connection method as will be apparent to one skilled in the art. When baroreflex activation device 70 is coupled to the switching mechanism 90, at least one electrode 71 will comprise an anode 76, and at least one electrode 71 will comprise a cathode 77. Various configurations of implantable electrodes for an implantable hypertension treatment device are described in U.S. Published Application No. U.S. 2004/0010303A1, commonly assigned to the assignee of the present invention, the disclosure of which is hereby incorporated by reference in its entirety.

Display 65 may illustrate which electrodes 71 are being activated, for example by having a display pattern or image which corresponds to the electrode array on baroreflex activation device 70. In one embodiment, display indicia 93 correspond to the location of electrodes 71 on baroreflex activation device 70. Those electrodes 71 connected to anode 76 may be illuminated in one color, and those electrodes 71 connected to cathode 77 may be illuminated in a second color.

Figure 9:
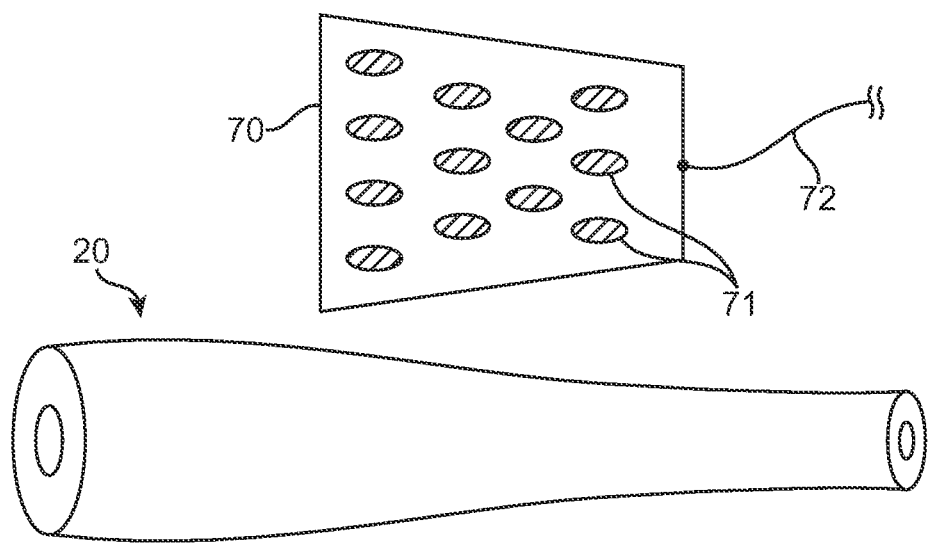
FIG. 9 is a perspective view of a tissue stimulation device according to an embodiment of the present invention.

Flexible base 73 of the electrode array 11 may comprise numerous possible shapes, configurations, and arrangements. For example, base 73 may comprise a square, rectangular, trapezoidal, tapered, triangular, circular, oblong, irregular, or any other shape suitable for the biological structure to which base 73 will envelop. One skilled in the art will appreciate the utility of various shapes depending on the circumstances. For example, a flexible base 73 having a trapezoidal or tapered shape is suitable for installation over an artery or other structure that narrows over its length, as a square or rectangular shaped flexible base 73 may not effectively envelop such a tapered profile. Such a tapered or trapezoidal flexible base 73 is depicted in FIG. 9. Additionally, flexible base 73 may comprise a hand-like shape, having multiple fingers configured to hold electrodes 71 and wrap around an artery, the fingers commonly joined on one end.

Figure 10:
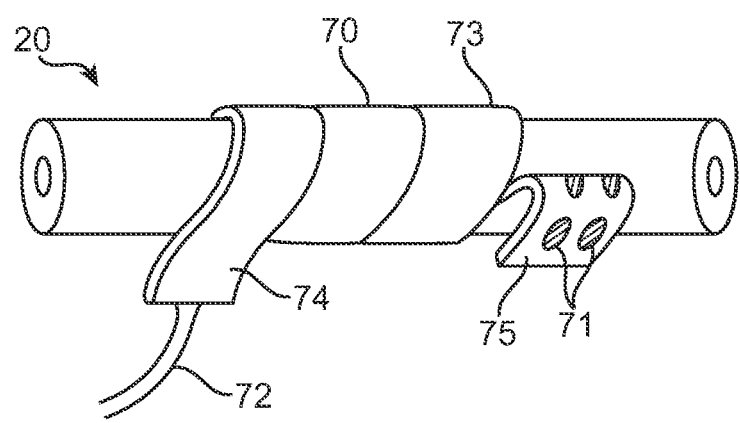
FIG. 10 is a perspective view of a tissue stimulation device according to an embodiment of the present invention.

Flexible base 73 may also comprise a helical shape, as depicted in FIG. 10. When installed on an artery, baroreflex activation device 70 spirals around the artery. In one embodiment, baroreflex activation device 70 can be cut to a desired length or shape, thereby accommodating a broad range of artery shapes and sizes.

Figure 11A:
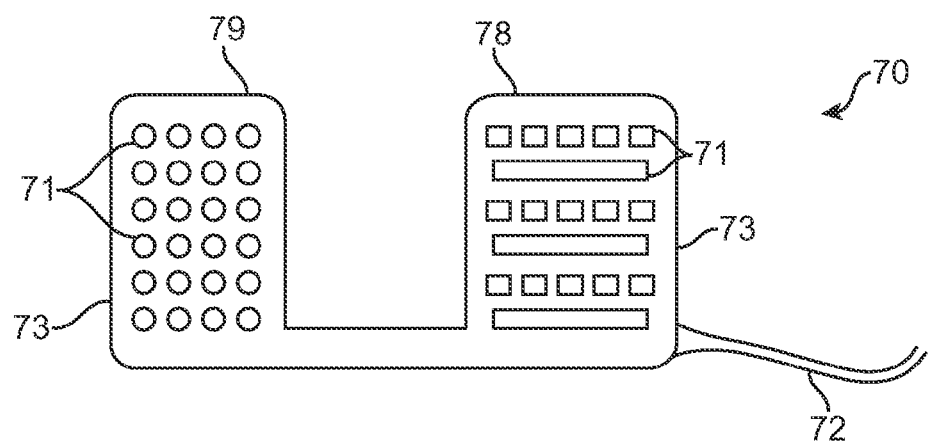
FIGS. 11a-11c are perspective views of tissue stimulation devices according to embodiments of the present invention.
Figure 11B:
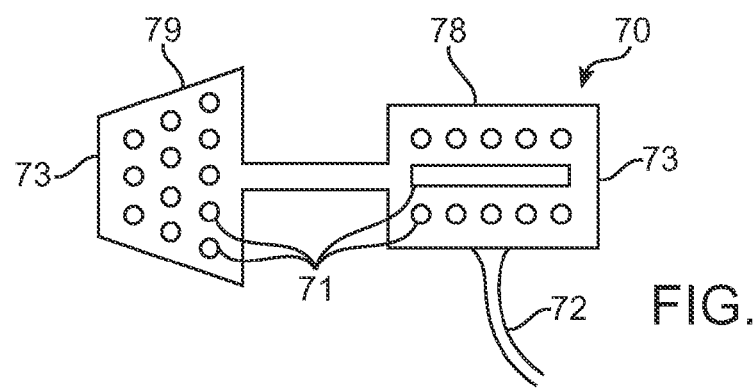
Figure 11C:
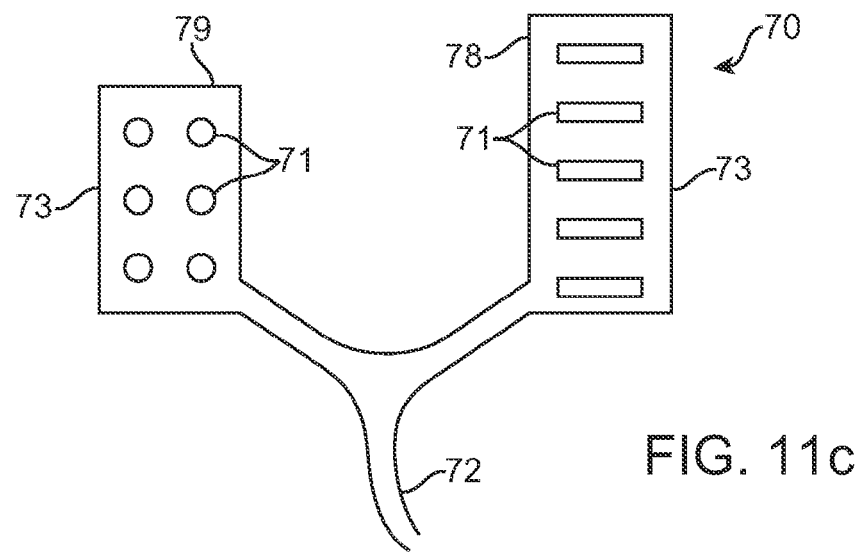

Referring now to FIGS. 11*a*-11*c*, a further embodiment of baroreflex activation device 70 is depicted, having two regions of electrodes 71. Base 73 comprises a first region 78 and a second region 79, each region having a plurality of electrodes 71. The sizes and shapes of regions 78 and 79 can be varied to suit various applications, and may comprise square, rectangular, or trapezoidal shapes, and various sizes. The shapes and sizes of baroreflex activation device 70 depicted in FIGS. 11*a*-11*c* should be considered merely illustrative, and not in any way limiting.

Just as flexible base 73 may be varied in size and shape, the present invention encompasses many possible configurations, shapes, sizes, and arrangements of electrodes 71. Electrodes 71 may be arranged symmetrically, asymmetrically, in rows and columns such as a N×N matrix, or randomly distributed on baroreflex activation device 70. Electrodes 71 may be evenly or unevenly spaced, and uniform or non-uniformly sized or shaped. Electrodes 71 may also be shaped and oriented in any way deemed suitable, including but not limited to circular, elliptical, square, rectangular, triangular, trapezoidal, arced, or any combination thereof. Electrodes 71 may also be grouped together in regions on electrode array 70, such as in FIGS. 11*a*-11*c*, such that all or part of a region of electrodes 71 may be activated simultaneously.

Additionally, electrodes 71 may comprise an arrangement whereby each electrode includes an anode center portion surrounded by a cathode ring, or a cathode center portion surrounded by an anode ring, such that the electrode comprises a point activation source.

Figure 14:
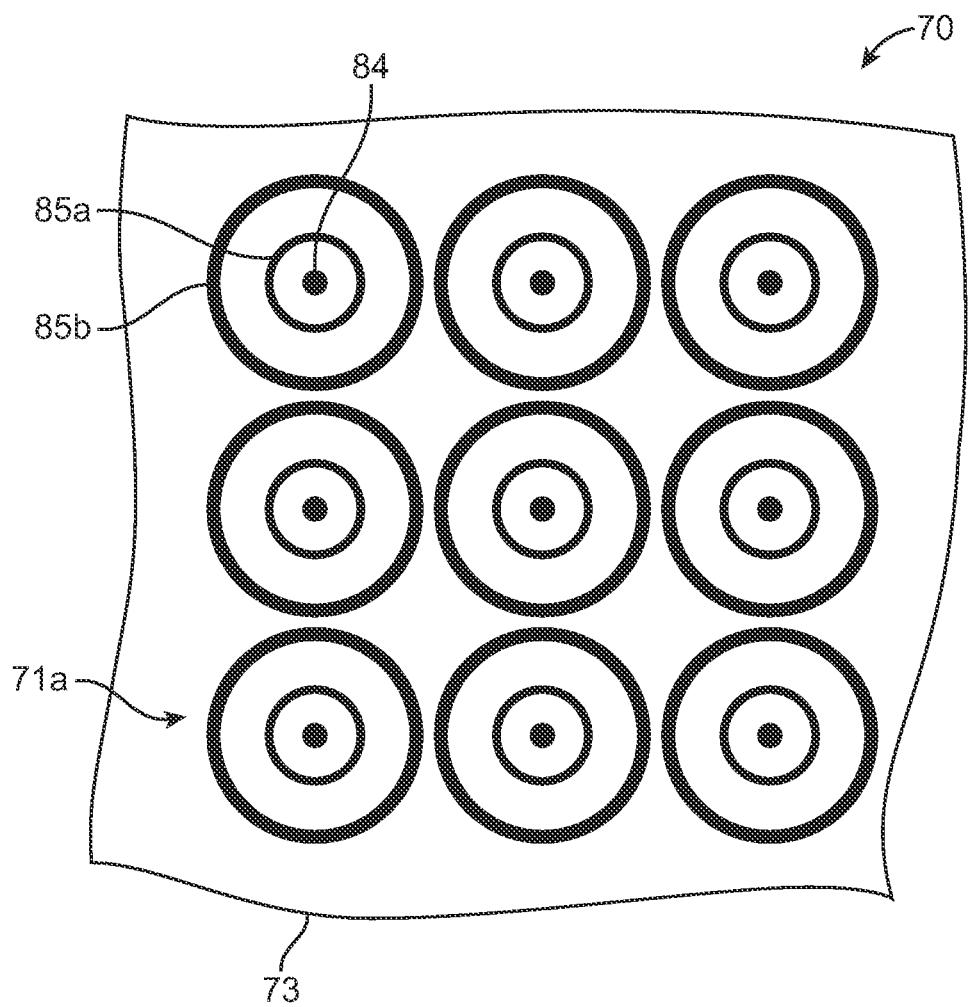
FIG. 14 is an illustration of a tissue stimulation device having multi-polar electrodes according to an embodiment of the present invention.

In one embodiment, electrode 71 may comprise a multi-polar electrode 71*a*, such as depicted in FIG. 14. Multi-polar electrode 71*a* includes a central portion 84, surrounded by two or more generally concentric outer rings 85*a*, and 85*b*. The polarities of center 84 and rings 85*a*, 85*b* may be set as desired, and may be switched as desired. Multi-polar electrode 71*a* may be configured to be tri-polar, quasi-polar, or more if desired.

Figure 12:
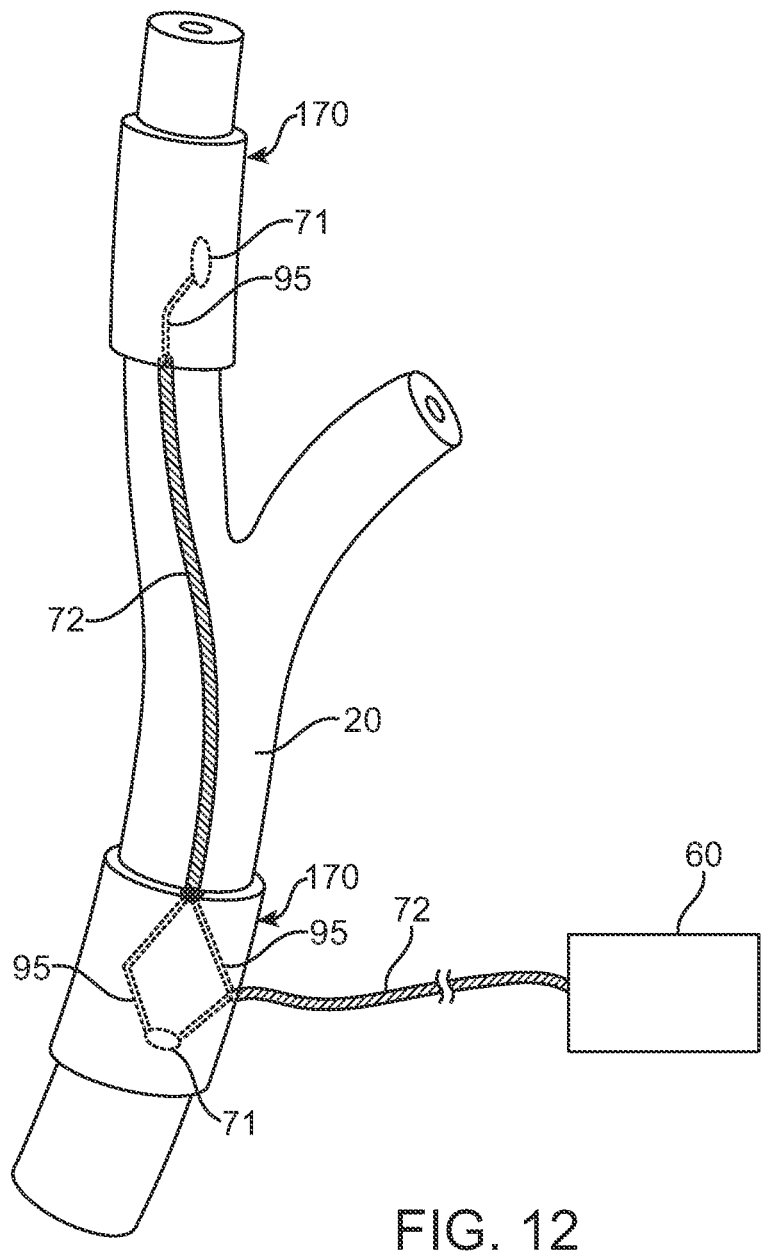
FIG. 12 is a perspective view of a tissue stimulation device according to an embodiment of the present invention.

Multiple baroreflex activation devices 70 may be used on a patient, such as depicted in FIG. 12. The multiple electrode arrays 70 may be operably coupled in series, parallel, or any combination of serial and parallel to control system 60, or each electrode array 70 may be coupled to a dedicated control system 60 (not shown).

In operation, pulse generator 66 generates a control signal, which is transmitted to switching mechanism 90. Control system 60 informs switching mechanism 90 which individual switches to open or close so as to activate the desired electrodes 71. The decision of which electrodes to energize may come from an algorithm stored in memory 62, user input 64, or sensor 80. Memory 62 may be adapted to store a library of switching patterns that can be used to operate switching mechanism 90. Sensor 80 may be used to provide data to control system 60 that will affect the switching pattern. Sensor 80 may be used as feedback to control system 60 such that a switching pattern will be modified based on the data provided by sensor 80, for example a physiological response to a switching pattern currently being implemented on a patient.

Control system 60 may then modify the switching pattern based on the data provided by sensor 80. Sensor 80 may also be coupled to user input 64.

Switching mechanism 90 may be arranged or incorporated in a variety of ways. In one embodiment, switching mechanism 90 may be integrated into or onto baroreflex activation device 70, reducing the complexity of large electrode arrays. In such an embodiment, the control signal is sent from signal generator 66 to switching mechanism 90 via cable 72. For each switchable electrode 71 or group of electrodes on baroreflex activation device 70, there must be a corresponding switch in switch mechanism 90, and a conductor 95 for each switch. Each conductor 95 may carry to each switch a control signal and a power signal, preferably using time-division multiplexing or frequency-division multiplexing. Appropriate multiplexers and demultiplexers are required in such an embodiment. In an alternate embodiment with switching mechanism 90 integrated into or onto baroreflex activation device 70, each conductor 95 comprises two distinct conductors, one for a control signal and one for power.

In a further embodiment of switching mechanism 90 being integrated into or onto baroreflex activation device 70, switching mechanism 90 may comprise a logic circuit having a bus-type architecture. Each individual switch contains a unique address, and bus messages contain an identifier to correspond to which switch needs to be activated or deactivated. The use of thin-film transistors and flexible printed circuitry in such an embodiment helps minimize the size of switching mechanism 90 and baroreflex activation device 70.

Anode 76 is switchably coupled to one or more electrodes 71, and cathode 77 is switchably coupled to one or more electrodes 71. Optionally, more than one electrode 71 is attached to the same switch output. Thus a single control signal may be sent to multiple electrodes 71 at the same time. Alternatively, a single control signal may be sequenced between different cathodes with the same anode, or between different anodes with the same cathode, in a windshield wiper-like pattern.

In another embodiment, switching mechanism 90 is integrated with signal generator 66. In such an embodiment, one conductor 95 is required for the control signal and one for power, for each electrode 71 on baroreflex activation device 70. Due to size limitations, this embodiment is limited in the number of electrodes 71 that can be provided on electrode array 70.

In another embodiment, switching mechanism 90 is switchably coupled to one or more multi-polar electrodes 71a. Anode 76 is switchably coupled to one or more multi-polar electrodes 71a, and cathode 77 is switchably coupled to one or more multi-polar electrodes 71a. Additionally, anode 76 and cathode 77 may be switchably coupled to one or more poles on multi-polar electrode 71a, such as for example anode 76 being coupled to an outer ring 85b and cathode 77 being coupled to inner ring 85a and center 84. Anode 76 and cathode 77 are preferably switchable among the poles of multi-polar electrode 71a.

In all embodiments of switching mechanism 90, it may be desirable to provide a backup set of switches to ensure continued operability of baroreflex activation device 70 in the event of a switch failure. In a further embodiment, switching mechanism 90 may include supercapacitors to provide enhanced power for each switch.

Referring now to the installation of baroreflex activation device 70, a surgeon wraps the device around a structure within a patient having baroreceptors 30, such as carotid sinus 20, and secures the device in a suitable manner. Exemplary structures and methods of securing baroreflex activation device may be found in U.S. patent application Ser. No. 11/695,210, entitled "Implantable Extravascular Vessel Electrostimulation System Having A Resilient Cuff," and U.S. patent application Ser. No. 11/766,592, entitled "Implantable Electrode Assembly Utilizing A Belt Mechanism For Sutureless Attachment," the disclosures of which are hereby incorporated by reference in their entireties. When installed on a biological structure such as carotid sinus 20, baroreflex activation device 70 circumferentiates the structure, surrounding some, most, or all of the outer surface of the structure. In one embodiment, electrodes 71 are in direct contact with the outer surface of the biological structure. However, electrodes 71 may be located within flexible base 73 such that the electrodes 71 are not in direct contact with the biological structure. Prior to the installation surgery, the surgeon will likely have a general idea of where baroreflex activation device 70 should be installed. However, the precise optimal location of the device is not usually apparent to the surgeon prior to, or at the time of, installation. Due to variations in the biological compositions (or tissue structure) in a particular area of a vessel, large variations exist in the effectiveness of a given baroreflex treatment due to variations in the pathways of current flow resulting from device placement.

The present invention simplifies the surgical installation of baroreflex activation device 70. By providing an electrode array 70 having a plurality of selectively activatable electrodes 71, different patterns or groups of electrodes 71 can be activated to produce different baroreflex responses in a patient. There are a number of methods of adjusting the baroreflex treatment, and for each adjustment method, a number of measurement methods.

In one embodiment, the baroreflex treatment may be adjusted as a part of the implantation surgery, after baroreflex activation device 70 has been installed on the desired biological structure. The surgeon causes baroreflex activation device 70 to activate different patterns of electrodes 71, thereby producing different baroreflex responses in the patient. The surgeon may select pre-programmed electrode activation patterns from a library contained in memory 62 of control system 60, or may generate his own patterns. In the case of generating original activation patterns, the surgeon is able to save desired patterns in memory 62 for use later. By being able to vary the electrode activation pattern, the need to reposition baroreflex activation device 70 during surgery is virtually eliminated.

In another embodiment, the baroreflex treatment can be easily modified or adjusted after baroreflex activation device 70 has been surgically implanted, by changing the electrode activation pattern on electrode array 70. The patient visits a physician who can load a different activation pattern from memory 62, or generate an original activation pattern.

In a further embodiment, the optimal treatment pathways within a patient may vary over time, thereby reducing the effectiveness of treatment at a given site. The present invention encompasses a method of adjusting a baroreflex treatment to counteract this, wherein the electrode activation pattern may be changed from a first pattern to a second pattern, the second pattern activating a combination of electrodes unique from the first pattern to stimulate different tissue. The second electrode activation pattern will produce a different baroreflex response in the patient than the first pattern. The different electrode activation patterns may be manually selected, or automatic. Automatic selection may be based on information received from a sensor, or based upon a schedule.

A number of measurements are provided in order to measure the response in a patient in response to a baroreflex treatment, to determine the efficacy of the treatment. In one embodiment, the patient's response can be directly measured with sensor 80. As discussed above, sensor 80 may measure blood pressure or other physiologic parameters. The data collected from sensor 80 is sent to control system 60 and used to analyze the efficacy of an applied baroreflex treatment. Measuring a patient's response with sensor 80 is suitable for all of the above methods of adjusting a baroreflex treatment.

In another embodiment, the efficacy of a baroreflex treatment is determined by utilizing sub-stimulation test signals on test subjects. To minimize the time necessary to map target locations of baroreceptors at a particular site within a patient, for example the carotid sinus 20, sub-stimulation test signals are transmitted to combinations or patterns of electrodes 71 on electrode array 70 and various signal attributes are measured. Attributes may include, but are not limited to, impedance, capacitance, current, power, and resistance. A preferred test signal, referred to as a sub-threshold or sub-stimulation signal, comprises a signal having characteristics not likely to cause a medically meaningful response in the baroreflex or nervous system of a patient or test subject. Such characteristics may include low voltage on the order of millivolts, low current on the order of milliamps, or high frequency outside of a range known to create a baroreflex response, or combinations thereof.

In one example, an electrode array 70 is implanted in one or more test subjects. Test subjects may be animals or humans. Stimulation signals are delivered to a portion or all of the possible electrode activation combinations, and the signal attributes associated with each possible electrode activation combination are measured. In addition, baroreflex response is measured in the test subject for at least some of the electrode activation combinations. In this way, a correlation among favorable signal attributes can be associated with favorable baroreflex responses for given electrode activation combinations.

The time necessary to measure a patient's response to a single baroreflex therapy delivered by baroreflex activation device 70 can take minutes. After a therapy has been delivered, additional minutes may be needed for the patient's baroreflex system to return to normal. If a physician wishes to test the patient's response to a broad range of electrode activation combinations, the time needed to do so will be measured in days or weeks. By utilizing sub-stimulation test signals, the time necessary to perform testing is greatly reduced. However, even mapping with sub-stimulation test signals can be extremely time consuming if electrode array 70 contains a large number of electrodes, for example more than sixteen, and if every possible electrode activation combination is desired to be tested. When mapping using sub-stimulation test signals, the number of effective electrode activation combinations may be based on the size and placement of individual selectively activatable electrodes 70 in relation to the size and location of baroreceptors 30 in carotid sinus 20. For example, if baroreceptors 30 are relatively large and electrodes 71 are relatively small, the number of electrode activation patterns that must be tested with sub-stimulation signals may be less than all possible electrode activation combinations, as there will be certain electrode activation combinations that are similar to one another. Because of this, the total number of electrode activation combinations to test may be reduced to only an effective number of electrode activation combinations.

Sub-stimulation signals are preferably delivered in as quick of succession as possible, in order to reduce the total amount of required testing time. Sub-stimulation signals may be delivered with a frequency of milliseconds, or even microseconds. One limit on the frequency at which sub-stimulation signals are delivered is the build-up of capacitance in vascular walls, for example. In one embodiment, the sequence of activation patterns can be varied to reduce capacitance buildup at any given portion of tissue being stimulated. Such capacitance may need to be dissipated before subsequent sub-stimulation signals are delivered. In one embodiment, sub-stimulation testing may be performed while the patient is asleep or under anesthetic, and therefore background activity levels are stable.

Data collected from test subjects is then used when implanting baroreflex activation device 70 in a patient needing baroreflex therapy. Upon installation, sub-stimulation test signals are sent to some or all of the possible electrode activation combinations, and the signal attributes associated with each possible electrode activation combination are measured. The measured signal attributes are analyzed by a computer, compared to the signal data from test subjects, and favorable signal attributes in the patient are identified. The identified favorable signal attributes correspond to favorable electrode activation combinations, and those favorable electrode activation combinations may then be selected to receive stimulation-level signals, either for therapy or for further refinement of combinations, in which case the patient's baroreflex response is measured in response to the stimulation-level signals for each of the selected electrode activation combinations. The time required to find an optimum electrode activation combination is therefore greatly reduced.

Optionally, the results produced by the automatic testing may be stored in memory 62 and the sub-stimulation test combinations may be repeated post-implant to confirm or alter the recommended electrode activation combination and polarities.

In a further embodiment, the use of sub-stimulation test signals is useful for optimizing electrode 71 shape and/or size. An electrode array 70 having electrodes 71 of different shapes and/or sizes may be implanted in a test subject, and sub-stimulation test signals are sent to electrode array 70, and the signal attributes measured. By comparing the signal attributes of electrodes having one shape/size against electrodes having a different shape/size, a favorable electrode design can be determined (such as determining the effectiveness of an electrode array 70 having sixteen round electrodes compared to the effectiveness of an electrode array having eight rectangular electrodes). Additionally, sub-stimulation test signals may be used to determine if more than one baroreflex activation device needs to be implanted.

In a still further embodiment of the present invention, a variable electrode activation combination is utilized. The electrode activation combination may be continuously variable or periodically variable. In the case of a continuously variable electrode activation combination, a standard random number generator, for example, may be coupled to control system 60. The random number generator supplies random combinations of anode-cathode electrode pairs, thereby creating continuously variable electrode activation combinations. Alternatively, pseudo-random patterns, or patterns based on chaos theory or game theory may be used. The electrode activation combination may also be periodically variable, wherein a period comprises a sequence of anode-cathode electrode activation combinations. The length of the period, and therefore the number of unique anode-cathode electrode activation combinations, may be adjusted, either automatically or manually, as desired. In one embodiment, the periodically variable electrode activation combination comprises the favorable electrode activation combinations identified from the sub-stimulation signal testing previously discussed.

Figure 13:
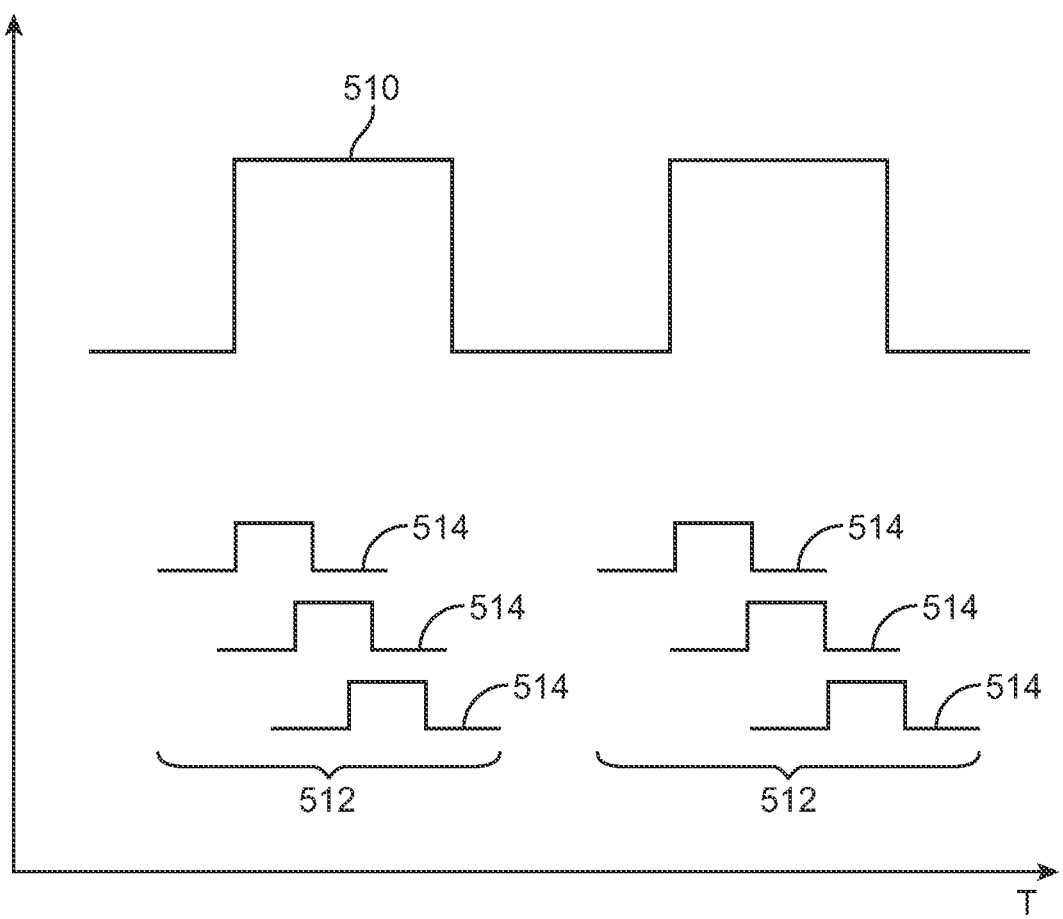
FIG. 13 is an illustration of a pulse series signal as a function of time.

In another embodiment of the present invention depicted in FIG. 13, the therapy generated by pulse generator 66 comprises multiple successive pulses. In contrast to a therapy comprising a single pulse waveform having a large amplitude, multiple pulses of smaller amplitude, referred to as a pulse series 512, are fired in succession. In one embodiment, each pulse 514 in the series 512 has a relatively smaller amplitude, thereby yielding a similarly effective result as compared to a larger pulse 510, however, less instantaneous power is required from the electronics, thereby conserving battery amperage requirements and potentially simplifying the pulse delivery electronics. Pulse series 512 may be fired between the same anode-electrode combination, in what would be referred to as a pulse train, or unique anode-cathode combinations may be used for each pulse in a pulse series 512. In one variation of this embodiment, each successive pulse 514 in the series 512 may be staggered so as to overlap, fired in a sequential timing manner or spaced apart with interval gaps between successive smaller pulses where the interval gaps would be significantly shorter than gaps between successive pulse sequences in the therapy. In another variation of this embodiment, successive pulses in a pulse series may be provided with the same or different waveshapes or waveforms.

In one embodiment of the present invention, a selected subset of the combination patterns are further validated by application of a threshold-level stimulation signal coupled with measurement of a surrogate feedback indication of the effect on the therapeutic parameter (blood pressure, nervous system activity, etc) of the stimulation-level threshold signal. Such indications may include, but are not limited to, nerve activity, or artifacts of an electrocardiogram tending to indicate the desired physiologic response corresponding to the stimulus. It will be understood that such a surrogate test pattern embodiment will take more time than the sub-stimulation signal testing embodiment, and depending on stimulation level, additional time between stimulation signals may be required to ameliorate stacking of a physiological response.

Figure 15:
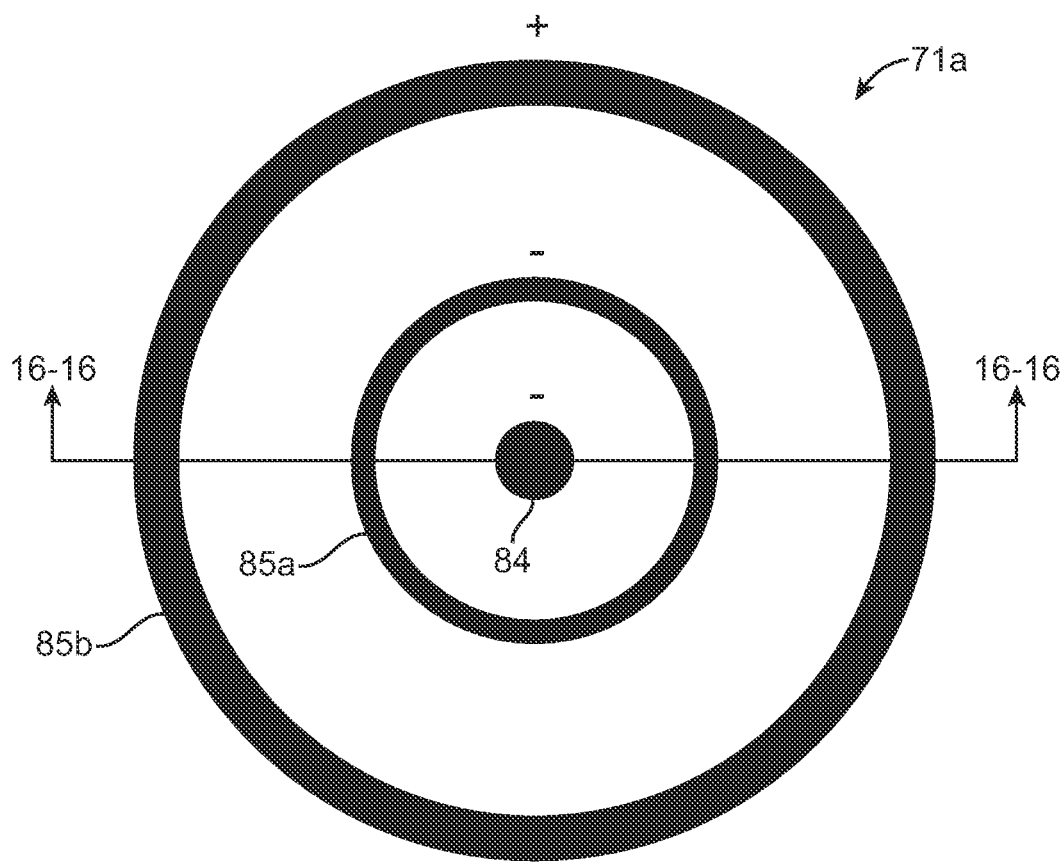
FIG. 15 is an illustration of a multi-polar electrode according to an embodiment of the present invention.
Figure 16:
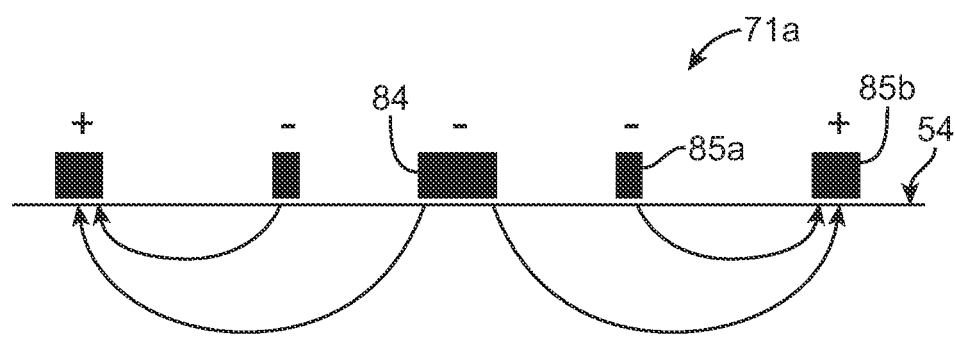
FIG. 16 is a cross-sectional view taken alone line 16-16 in FIG. 15.

In another embodiment of the present invention, baroreflex activation device 70 includes a plurality of multi-polar electrodes 71a, each electrode 71a having a center 84 and two or more surrounding rings 85a, 85b, as depicted in FIGS. 14, 15, and 16. Multi-polar electrode 71a is adapted to deliver a baroreflex therapy having a non-directional, yet spatially limited stimulation. A non-directional stimulation is one in which the distribution of the electric field is not affected by rotation or orientation of the electrode assembly. Electrodes 71a are preferably secured to flexible base 73, and may be flush with flexible base 73 or part or all of electrode 71a may protrude from base 73, and may protrude into the tissue. Additional rings may be provided in multi-polar electrode 71a, such as to create a quasi-polar electrode. The electrical field emitted from electrode 71a expands in a quasi-homogenous and controlled manner, such that the region of tissue stimulation may be precisely controlled.

Figure 18:
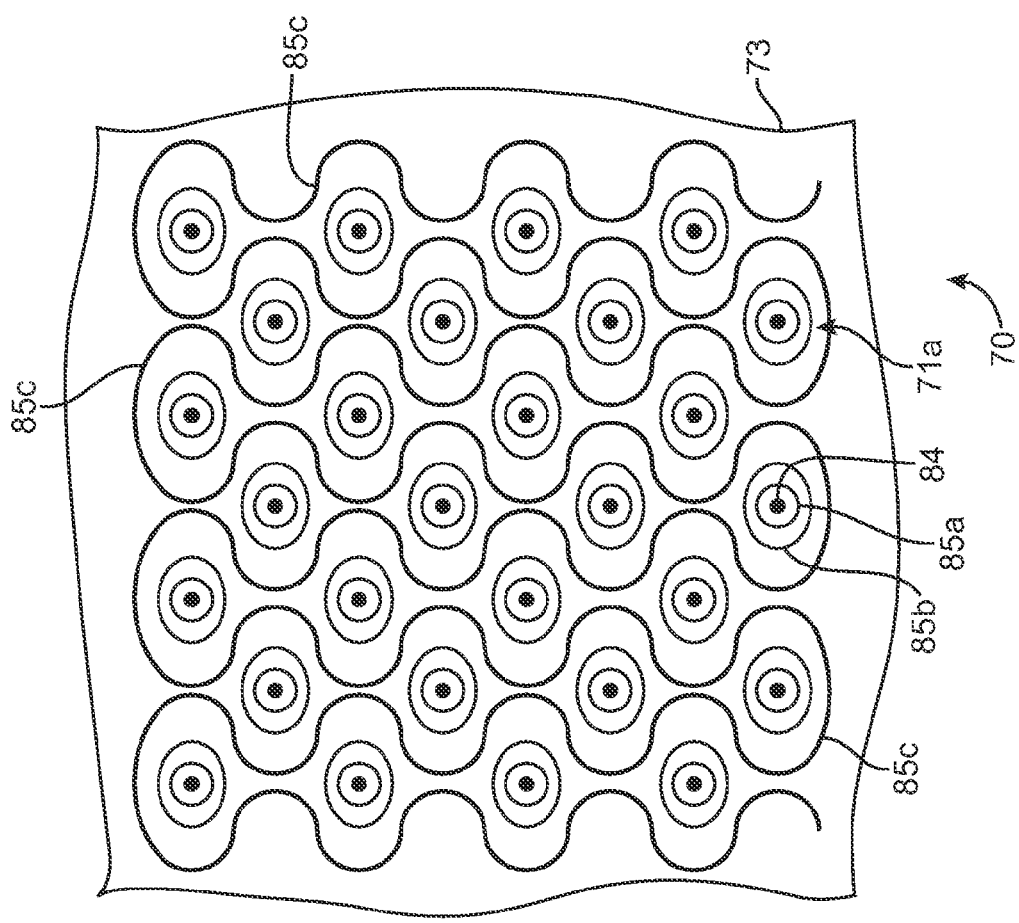
FIG. 18 is an illustration of a baroreflex activation device having shielded multi-polar electrodes according to a further embodiment of the present invention.
Figure 17:
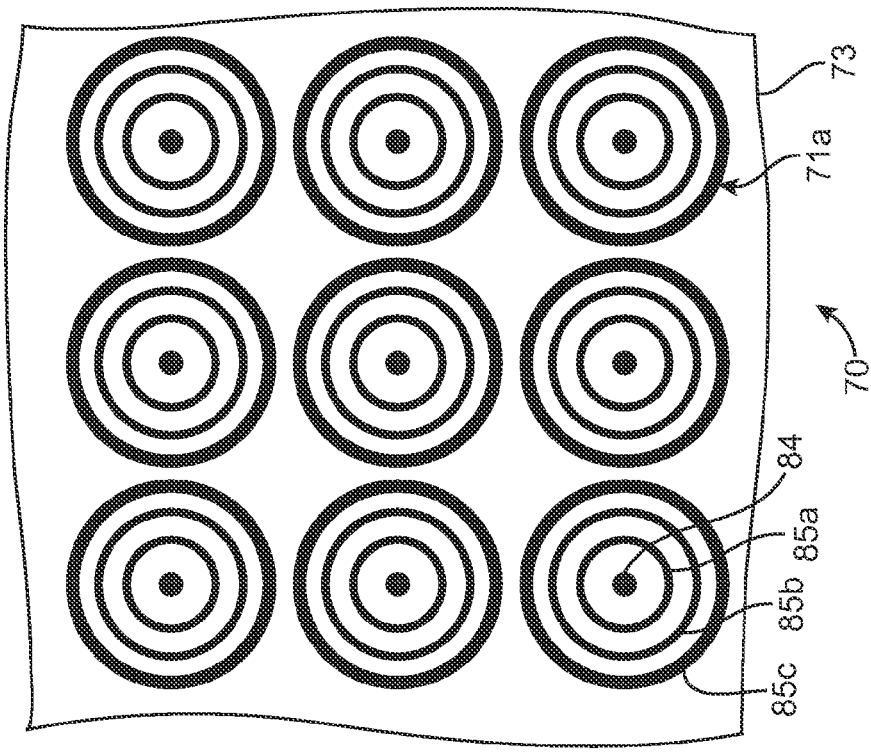
FIG. 17 is an illustration of a baroreflex activation device having shielded multi-polar electrodes according to an embodiment of the present invention.

In one embodiment depicted in FIG. 17, electrode 71a includes a shielding portion or return path 85c, surrounding electrode 71a and creating a ground plane between neighboring electrodes. Shielding portion 85c may comprise a concentric ring, similar to rings 85a and 85b. Alternatively, shielding portion 85c may comprise a continuous structure secured to base 73 and configured to shield electrodes from one another, as illustrated in FIG. 18.

An example of how a multi-pole electrode 71a may operate follows. Center portion 84 and inner ring 85a are held at a controlled potential with respect to outer ring 85b. In one embodiment, outer ring 85b may comprise ground. Such an arrangement forces the current path to extend into the tissue (of a vessel 54, for example), as illustrated in FIG. 16. The depth of the current, and therefore depth of the electric field, is determined by a number of factors, including but not limited to: the relative distance between center 84, inner ring 85a, and outer ring 85b; the surface area ratio between inner ring 84a and outer ring 84b; the potential between center 84, inner ring 85a, and outer ring 85b; and the distribution of a single electrode 71a among other electrodes in an array. By modifying these factors, the shape, area, and/or depth of the electric field can be tailored to the desired application.

The structure of multi-pole electrode 71a provides a sharper delimitation of the electric field during stimulation, as compared to an embodiment where two or more separate electrodes 71 are used to conduct current across a vessel. Such delimitation minimizes extraneous tissue stimulation, and can allow for a broader stimulation area due to the sharp edge control of the activation region. In one embodiment, it may be desirable to provide a stimulation at a certain depth within the tissue. For example, wherein tissues are arranged in layers, such as in the walls of a blood vessel, the present invention may be configured to selectively stimulate one or more layers of tissue, while not stimulating other layer(s) of tissue. In another embodiment, the present invention may be configured to control the current density in a designated volumetric region with the use of one or more electrodes 71a, wherein the volumetric region includes one or more tissue areas desired to be activated or otherwise stimulated.

Figure 19:
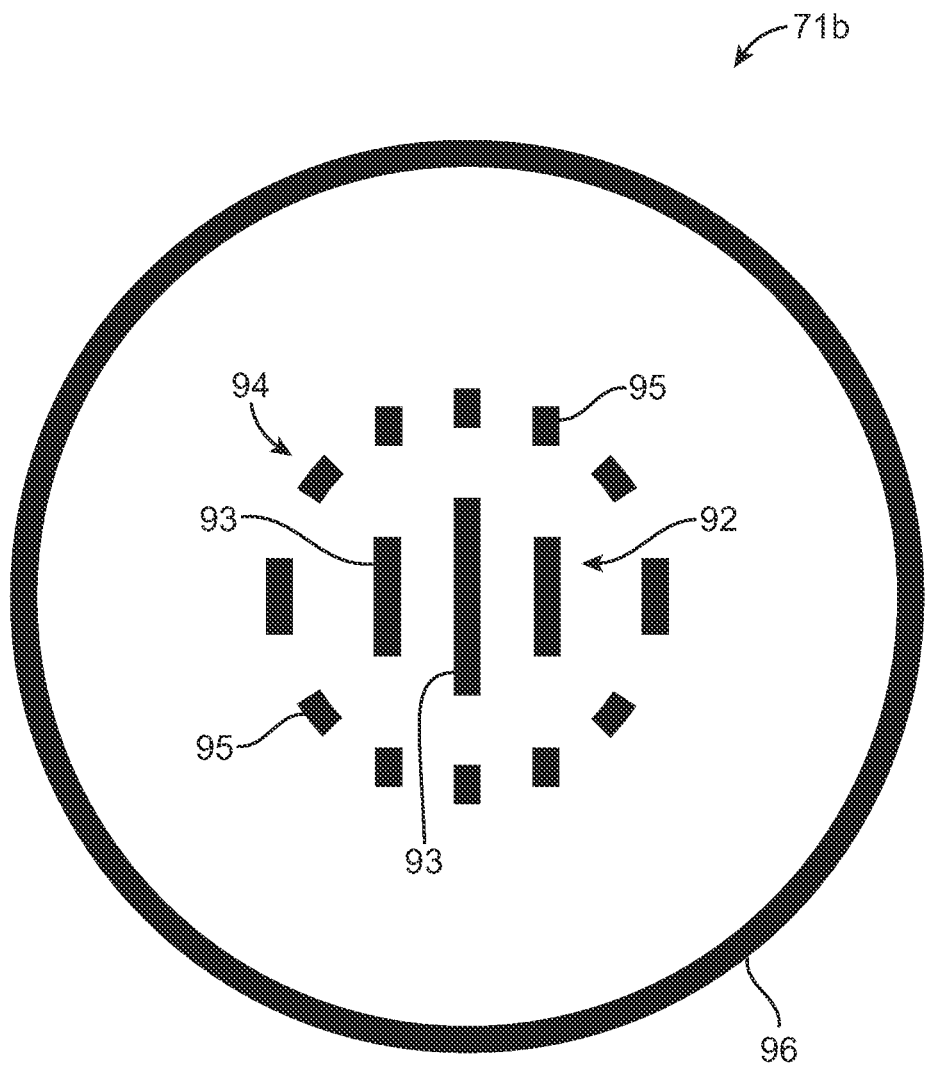
FIG. 19 is an illustration of a multi-polar electrode according to an embodiment of the present invention.

A further embodiment of an electrode to be used in the present invention is electrode 71b, depicted in FIG. 19. Multi-polar electrode 71b comprises a center portion 92, at least one inner ring 94, and an outer ring 96. In one embodiment, center portion 92 comprises a plurality of electrode segments 93, each segment 93 of center portion 92 being electrically common. In one embodiment, inner ring 94 may comprise a plurality of electrode segments 95 arranged in a ring-like configuration, each segment 95 of inner ring 94 being electrically common. Outer ring 96 may also comprise a plurality of electrode segments (not shown).

Electrode segments in the various portions of electrode 71b may allow the electrode to be more easily manufactured. Additionally, the lifespan of electrode 71b may be increased, due to the reduced chance of material fatigue in rings comprised of segments. Electrode 71b may also provide higher current density in an area being stimulated. In one embodiment, electrode 71b may have less surface area for an inner segmented ring 94 as compared to an inner ring of electrode 71a. The current density from electrode 71b will be greater than the current density from electrode 71a for a given applied current.

One or more characteristics of electrode 71b may be adjusted during the manufacturing process to alter one or more parameters of the delivered therapy. For example, the size of the various rings and center portion, the ratios of sizes amongst the rings and center portion, the segment sizes in the rings and/or center portion, the spacing of segments, and the distances between the rings and/or center portion.

A pre-clinical study was conducted on mammal test subjects, wherein one group of test subjects was given a therapy using one or more electrodes 71, and another group of test subjects was given a therapy using one or more electrodes 71b. The group having electrodes 71 required significantly more power, current, and voltage to achieve an identical reduction in blood pressure as the group having electrodes 71b.

Multi-pole electrodes 71a and/or 71b may be substituted for electrode 70 in any or all of the embodiments disclosed herein. In particular, multi-polar electrodes 71a and/or 71b may be used with sub-stimulation test signals. As part of a mapping process, the sub-stimulation test signals may be used to test different electrode activation patterns on a single multi-polar electrode 71a or 71b, by testing different combinations of stimulations between the center, inner ring, and outer ring. While the present invention has been described with particular reference to an intravascular baroreflex activation device 70, it should be understood that embodiments of the present invention may also be applied for baroreflex devices adapted to be utilized in intravascular, transvascular, and even about the vascular sheath surrounding both the artery and vein, each of which will be briefly described.

An intravascular baroreflex activation device may comprise a stent-like structure, having a plurality of electrodes 71 in accordance with the matrix designs as have been described. A transvascular baroreflex activation device may be disposed substantially within a vein, such as the jugular vein, with one or more electrical leads passing from the vein to an adjacent artery, such as the carotid sinus, or simply transmitting energy across the venous wall to the adjacent arterial wall. The one or more leads may protrude into the wall of the adjacent artery, or may remain on the exterior of the artery. A baroreflex activation device may be adapted for placement around all or a portion of a vascular sheath structure surrounding at least one vein and one artery as well as associated nerve structures. In this embodiment, the baroreflex activation device may take any of the configurations described for the extravascular embodiments but with a corresponding diameter to match the diameter of the sheath.

Further, while the present invention has been described with particular reference to embodiments wherein baroreflex activation device 70 is an electrical device, it should be understood that non-electrical embodiments are encompassed by the present invention. For example, baroreflex activation device 70 may comprise a matrix of micro electro mechanical systems (MEMS) based devices. The baroreflex system may be mechanically activated in order to stimulate a patient's baroreflex system. Additionally, baroreceptor activation device 70 may comprise a matrix of piezoelectric devices, wherein each piezoelectric device receives an input voltage and changes shape in response to the input voltage. The change in shape of the piezoelectric devices would stimulate the baroreflex response of the patient.

The optimization methods discussed above may be useful in additional applications. For example, in an embodiment where baroreceptor activation device 70 is used in conjunction with one or more other implantable medical devices having a sensing capability (such as a defibrillator or cardiac pacemaker), the optimization methods discussed herein can be used to minimize crosstalk, or signal interference, between the devices. Additionally, in an embodiment of the present invention wherein electrodes 71 are adapted to sense a physiologic signal or parameter (such as the parameters discussed above in relation to sensor 80), the optimization methods disclosed herein may be used to optimize the sensed parameter.

Although the present invention has been described with reference to particular embodiments, one skilled in the art will recognize that changes may be made in form and detail without departing from the spirit and scope of the invention. Therefore, the illustrated embodiments should be considered in all respects as illustrative and not restrictive.

What is claimed is:

1. A method, comprising:
    implanting a baroreflex activation device chronically within a patient, the device including a plurality of independently activatable electrodes and being implanted in or on a blood vessel such that the independently activatable electrodes are proximate one or more baroreceptors in a wall of the blood vessel;
    delivering a sub-stimulation signal to a first pattern of one or more of the electrodes, the sub-stimulation signal having a voltage, current and/or frequency selected so as not to create a medically meaningful baroreflex response in the patient;
    measuring one or more attributes of the sub-stimulation signal delivered to the first pattern of electrodes;
    delivering a second sub-stimulation signal to a second pattern of one or more of the electrodes, the second pattern differing from the first pattern;
    measuring one or more attributes of the second sub-stimulation signal delivered to the second pattern of electrodes;
    comparing the attributes measured from the sub-stimulation signals to attributes of signals known to cause favorable baroreceptor activation; and
    selecting at least one pattern of one or more electrodes for delivering a baroreflex therapy based on the measured attributes of the sub-stimulation signals.

2. The method of claim 1, further comprising delivering a baroreflex therapy with the at least one selected pattern, the baroreflex therapy including a stimulation-level signal configured to create a measurable patient response.

3. The method of claim 2, further comprising:
    measuring one or more patient parameters indicative of a response to the delivered therapy; and
    confirming or altering the selected pattern based on the measured one or more patient parameters indicative of a response.

4. The method of claim 1, further comprising:
    storing a plurality of possible favorable patterns of electrodes;
    implanting a medical device configured to deliver a baroreflex therapy in a second patient;
    activating the plurality of patterns individually with sub-stimulation signals;
    measuring one or more attributes of the sub-stimulation signal for a specific pattern in the second patient;
    accessing the stored one or more signal attributes;
    correlating the one or more measured signal attributes in the second patient to the stored one or more signal attributes;
    selecting one or more patterns for therapy based on the measured signal attributes and the stored signal attributes.

5. The method of claim 1, wherein measuring one or more attributes of the sub-stimulation signal comprises measuring one or more attributes selected from the group consisting of: impedance, capacitance, current, power, and resistance.

6. A method of providing a system for baroreflex activation therapy, comprising:
    manufacturing a baroreflex activation device and making it available to a user, the device having a plurality of independently activatable electrodes; and
    providing instructions to the user for implanting the system, comprising:
        implanting the baroreflex activation device chronically in or on a blood vessel such that the independently activatable electrodes are proximate one or more baroreceptors in a wall of the blood vessel;
        delivering a sub-stimulation signal to a first pattern of one or more of the electrodes, the sub-stimulation signal having a voltage, current and/or frequency selected so as not to create a medically meaningful baroreflex response in a patient;

measuring one or more attributes of the sub-stimulation signal delivered to the first pattern of electrodes;

delivering a second sub-stimulation signal to a second pattern of one or more of the electrodes, the second pattern differing from the first pattern;

measuring one or more attributes of the second sub-stimulation signal delivered to the second pattern of electrodes;

comparing the attributes measured from the sub-stimulation signals to attributes of signals known to cause favorable baroreceptor activation; and selecting at least one pattern of one or more electrodes for delivering a baroreflex therapy based on the measured attributes of the sub-stimulation signals.

7. The method of claim 6, wherein providing instructions further comprises: delivering a baroreflex therapy with the at least one selected pattern, the baroreflex therapy including a stimulation-level signal configured to create a measurable patient response.

8. The method of claim 7, further comprising:
measuring one or more patient parameters indicative of a response to the delivered therapy; and confirming or altering the selected pattern based on the measured one or more patient parameters indicative of a response.

9. The method of claim 6, the instructions further comprising:

storing a plurality of possible favorable patterns of electrodes;

implanting a medical device configured to deliver a baroreflex therapy in a second patient;

activating the plurality of patterns individually with sub-stimulation signals;

measuring one or more attributes of the sub-stimulation signal for a specific pattern in the second patient;

accessing the stored one or more signal attributes;

correlating the one or more measured signal attributes in the second patient to the stored one or more signal attributes;

selecting one or more patterns for therapy based on the measured signal attributes and the stored signal attributes.

10. The method of claim 6, wherein measuring one or more attributes of the sub-stimulation signal comprises measuring one or more attributes selected from the group consisting of: impedance, capacitance, current, power, and resistance.

* * * * *

UNITED STATES PATENT AND TRADEMARK OFFICE
CERTIFICATE OF CORRECTION

PATENT NO. : 8,620,422 B2  
APPLICATION NO. : 11/862508  
DATED : December 31, 2013  
INVENTOR(S) : Robert S. Kieval et al.

Page 1 of 1

It is certified that error appears in the above-identified patent and that said Letters Patent is hereby corrected as shown below:

<u>On the Title Page, List of Inventors, item 75</u>
Delete "Adam Cates, Minneapolis, MN (US)"
Delete "Alejandro Covalin, Los Angeles, CA (US)"

Signed and Sealed this
Fourth Day of March, 2014

Michelle K. Lee
*Deputy Director of the United States Patent and Trademark Office*